United States Patent [19]

Zheng

[11] Patent Number: 5,260,067
[45] Date of Patent: Nov. 9, 1993

[54] CYTOTROPIC HETEROGENEOUS MOLECULAR LIPIDS (CHML) AND PROCESS FOR PREPARING THE SAME

[76] Inventor: Xu Zheng, 3865 Wilson Blvd., Suite 202, Arlington, Va. 22203-1919

[21] Appl. No.: 824,927

[22] Filed: Jan. 23, 1992

Related U.S. Application Data

[63] Continuation-in-part of Ser. No. 803,738, Dec. 9, 1991, abandoned, which is a continuation of Ser. No. 435,882, Nov. 14, 1989, abandoned.

[30] Foreign Application Priority Data

Nov. 16, 1988 [CN] China ................... 88108000

[51] Int. Cl.$^5$ ............. A61K 37/22; A61K 31/59; A61K 31/595; A61K 31/355
[52] U.S. Cl. ................. 424/450; 514/167; 514/168; 514/458; 514/560; 514/558; 514/573; 514/972
[58] Field of Search .......... 424/450; 514/167, 168, 514/458, 560, 558, 573, 972

[56] References Cited

U.S. PATENT DOCUMENTS 4,921,705 5/1990 Arai et al. ..................... 424/450

OTHER PUBLICATIONS

Gu Xuequi, et al.: Introduction of Polyphase Liposome A Promosing Carrier for Chemotherapeutic Agents, Research Bulletins and Abstract for FIrst Beijing Int'l Symposium on Cancer Chemotherapy, Sep. 7-9, 1986, Beijing, China.
Liu Guo-jie. Yao Ji Xue (pharmaceutics). Second edition. People's publishing house. Beijing. 1985; pp. 992-993.
Gu-Xue-qin. Yao Wu Zhi Ji Xi Ji Xung Xuan Bian (selected edition of new types of pharmaceutics). People's health publishing house, Beijing. 1984 p. 123.
Ren Min Zheng Xie Bao (newspaper of People's political consultative conference) 1984, Nov. 12.
Mar X, J. L. Liposomes: research applications grow Science 1987; 199:1056.
Gregoriadis, G. The carrier potential of liposomes in biology and medicine N. Engl. J. Med. 1976; 295:704,765. Parts I and II.
C. R. Alving. Lipsome Techniques in Cell Biology. Nature 1987; vol. 330, 1189.

*Primary Examiner*—Frederick E. Waddell
*Assistant Examiner*—K. Weddington
*Attorney, Agent, or Firm*—Armstrong, Westerman, Hattori, McLeland & Naughton

[57] ABSTRACT

A series of cytotropic heterogeneous molecular lipids (CHML) and the method of preparation thereof are disclosed in the invention. CHML provided by this invention is in molecular type, it is an activated molecular carrier of functions with orientionally penetrating into membranes or walls of the cells. It possesses the active site for binding anti-carcinogenic drugs which is water soluble, lipid soluble or gas soluble and possesses the activated portion for binding structure of membrane of cancer cells also.

CHML can synergetically injure the carcinoma cells and varius verus, at the same time it can enhance the immunity of the body. These are ascertained by the animal tests and in vitro tests.

CHML in this invention can kill the sarcoma cell S-180 within 50 min. and the cells of human squamous cell carcinoma of esophagus within 40 min.

The rate of DNA and RNA depolymerizations in cancer cells and mortality of cancer cells are attained to 100%. These are evidenced in the vitro test also.

4 Claims, 6 Drawing Sheets

CYTOTROPIC HETEROGENEOUS MOLECULAR LIPIDS (CHML) AND PROCESS FOR PREPARING THE SAME

This application is a continuation-in-part to application Ser. No. 07/803,738; filed Dec. 9, 1991; now abandoned, which is a continuation of U.S. Ser. No. 07/435,882, filed Nov. 14, 1989; now abandoned.

This invention relates to lipids, particularly to a series of what is referred to herein as Cytotropic Heterogeneous Molecular Lipids and to a process for preparing the same.

BACKGROUND OF THE INVENTION

In the early 1960's, British Scientist Bangham and others found that phosphatide may form small multilayered capsules while dispersing in water, and discovered that each layer of bimolecular lipids in a multilayer cyst is separated by water, the thickness of each layer being about 40 Å. This kind of capsule formed of microparticles, having a structure similar to a biomembrane, is termed a liposome.

Since liposomes comprise a hydrophilic and/or lipophilic "small room", these "small rooms" may envelope molecules and ions which are soluble in water or lipid. Due to these specific characteristics, liposomes can be useful as a carrier, especially for pharmaceuticals. Further, liposomes may alter the mechanism of pharmaceutical metabolism and selectively transport the pharmaceutical to the "target", then release the pharmaceutical at the proper part of tissues to be cured. Thus, toxicity to normal cells can be reduced and the curative effect, i.e. attack on deleterious cells, can be greatly enhanced. In addition, there is another specific property in that the pharmaceutical enveloped by the liposome may be slowly released into local sites whether entering into blood circulation or combining with cells and tissues, even entering into cells through pinocytosis. With the slow release mechanism of liposomes, the half-life of the effective pharmaceutical is prolonged and the therapeutic effect is obviously improved. Furthermore, liposomes are made from natural phosphatides and cholesterols, having low toxicity, free from immunogens and with suitable bio-compatibility and bio-degradable properties. Recently, liposome engineering has made progress and the application of liposomes as a carrier for pharmaceuticals has been promoted.

In 1971, British scientist Ryman and others suggested that liposomes could be used as a carrier for enzymes or pharmaceuticals. Based on research of biomembrane theory, Ryman started to envelop enzymes or pharmaceuticals into liposomes, in order to protect for the active substances or pharmaceutical from destruction in blood circulation and to selectively attack the deleterious cells of the target tissue.

Chinese Canadian scientist Chang Ming-Su has researched liposome carriers of pharmaceuticals for therapic usage. In 1985, a famous Chinese Professor, Gu Xue-qiu, got the highest honor at the Fourth International Cancer of Lungs Conference for reporting the success, in the 1980's, of two kinds of polyphase liposomes as anti-cancer pharmaceutical carriers in combination with other chemical drugs to combat cancer.

Polyphase liposomes are new forms of anti-cancer pharmaceutical carriers of a polyphase-dispersing system. By enveloping some anti-cancer pharmaceutical into the carrier, and administering it into the blood circulation of the patient by intravenous injection, the polyphase liposome can exactly hit the target cancer tissue as a so-called "ultra-micro missile". The polyphase liposome is of a milky-white emulsion. Several kinds of emulsive intravenous injections which have been developed are composed of ultra-micro particles of a drug carrier, having a lymph system orientation, some of them penetrating the lysosome through phagocytosis of the phagocyte of dicty endothelial system, upon which the pharmaceutical is released upon digesting. Others release the pharmaceutical upon digesting by means of a fusion function, namely, due to the liposome membrane being similar to that of the cell membrane, the polyphase liposome fuses into the cell, thus maintaining a rather high concentration of the drug in the target tissue Such an orientation significantly reduces the toxicity and attack of anti-cancer pharmaceuticals on normal cells. As such, the therapic effect of the anti-cancer pharmaceutical will be enhanced while the toxicity to the normal cells is reduced.

In general, a liposome may be deemed to be an artificial membrane of cell, having an enclosed spheroidal structure (i.e., a "smallroom") with a diameter of about 300-2000 Å and a maximum diameter of about $5\mu$. Liposomes having relatively large diameters cannot penetrate into the cytoplasm directly. In such cases, it is necessary for the liposome to be phagocytized by the cell.

Up to the present, there have been in the prior art liposomes which mostly comprise phosphatide as a skeleton material and additives. Phosphatide is an amphoteric compound possessing hydrophilic and lipophilic radicals, including natural phosphatide (lecithin and soy-bean) and synthetic phosphatide (such as phosphatidyl choline, dipalmitol phosphatidyl choline and distearyl phosphatidyl choline). These phosphatides provide two hydrophilic chains. They form liposomes of bimolecular layers in water, no matter how the structure of the hydrophilic radical is. The additives used in the prior art are, for example, cholesterol, octadecamine and phosphatidate, etc. Although cholesterol is useful for regulating the flowability and permeability of a bimolecular layer, cholesterol is not good for human beings. Octadecamine and phosphatidate may be used to alter the surface electrical charges of a liposome. The components of a polyphase liposome may be phosphatide, oleic acid, cholesterol and nonionic surfactants such as PVP (polyvinylpyrrolidone).

Much research work has been directed to liposomes as drug carriers, as models of bio-membranes, and methods of preparation. Polyphase liposomes are formed after the phosphatides contact with water. Formation is due to the action if its polar group and hydrophobic group which lead to the formation of poly bimolecular layers of a closed type spherical structure. The water layer is laid between the bimolecular layers as the water-soluble drugs are enveloped into it, the liposoluble pharmaceutical being enveloped in the bimolecular layers. Many factors as surface characteristics, particle sizes, differences in forms, surface electrical charges of the liposome can effect the stability in vivo and the percentages of enveloped pharmaceutical. The factors depend upon the components of phosphatides and methods of preparation.

Chemical properties of phosphatide with unsaturated fatty acid chain, such as of lecithin and soya bean lecithin are sometimes not sufficiently stable. Phosphatide is susceptible to oxidation and hydrolysis. Thus, peroxides, propanediol and lysophosphatide are produced. The oxidation of lecithin will subject the membrane formed to decreased flowability and increased stability and negative electrical charge conditions. Thus leakage of drugs will be promoted so that retaining of drugs will become less and the liposome will be easily aggregated and precipitated, thereby producing toxicity. Therefore, it has been suggested that lecithin as a membrane material should have high purity and an oxidation index of less than 0.2.

In preparation of liposomes it is a difficult problem to envelope a large quantity of drug. For example, where the liposolubility and aqueous solubility of the pharmaceutical are both low, the envelopment quantity of the drug will be less. And where the molecule of the drug is small and easily subject to percolation, the envelopment quantity of the drug will be weaker.

In the prior art, generally speaking, it has been known that a liposome or a polyphase liposome possesses advantages as a carrier for pharmaceuticals. For example, they may enter into cells as a carrier of a pharmaceutical, enabling the pharmaceutical to maintain its therapeutic effect for a prolonged period of time since the pharmaceutical enveloped by the carrier will avoid destruction in the blood circulation. During preparation, pharmaceuticals which may be hydrophilic or lipophilic can be enveloped. They may be formulated as "water in oil" or "oil in water" type emulsions, so that they may be phagocytized by cells through phagocytosis when they touch the surface of the cells. Furthermore, due to their lymph system orientation and selectivity, the amount of their entering into the lymphoglandulae, which is full of dicty endothelium cells, will be large, etc. However, in the data reported in the prior art there are some shortcomings at the present time in liposome or polyphase liposome, such as that their particle sizes formed are relatively large (about ten times bigger than the CHML of present invention), and that the fact they might cause systemic capillary circulation obstacle when they enter the vein. Further, they should be phagocytized by cells to enter them, thus there must be an energy consumption in the cells. In addition, their idiosyncratic phagocytosis by deleterious cells system in cancer cells is not so strong that they shall be often phagocytized by normal cells, causing the normal cells to be poisoned and the bioeffect of the pharmaceutical to be reduced. Also, their promotion of immunocytes of human beings is seldom reported in the prior art. They could not envelop two or more phases of pharmaceutical in the same layer. Finally, they may contain cholesterol and polyvinyl pyrrolidone (PVP) which exert unhealthy effects to human beings, etc.

SUMMARY OF THE INVENTION

In view of the foregoing, the main object of this invention is to provide a series of lipids with very small size, on the order of molecular dimensions, which have an active orientation so as to penetrate into the membrane or wall of cells, and having relatively high idiosyncratic absorbing capacity by target cells, so as to function as a "molecular missile" carrying only as small an amount of pharmaceutical as is necessary.

Another object of this invention is to provide such a series of lipids on the order of molecular dimension, comprising no phosphatide plus cholesterol system, thus not having any disadvantageous factors from that system.

A further object of the invention is to provide such a series of lipids on the order of molecular dimension, comprising no phosphatide plus cholesterol system, which itself has the effect of promotion for the immunity function of human beings per se, and which itself has the effect of killing off cells of therioma or virus.

A further object of the invention is to provide a process for preparing the lipids described above.

Other and further objects, features and advantages of the invention will appear more fully from the following descriptions.

(a) smears of control: S-180 sarcoma cell counting = $5 \times 10^6$/ml. 50 min $\times$ 350.

(b) smears of experimental tube: S-180 cell counting = $5 \times 10^6$/ml, 1 mg of CHML-Y solution is added. 10 min $\times$ 350.

(c) Smears of experimental tube: S-180 cell counting = $5 \times 10^6$/ml, 1 mg of CHML-Y solution is added. 20 min. $\times$ 350.

(d) Smears of experimental tube: S-180 cell counting = $5 \times 10^6$/ml, 1 mg of CHML-Y solution is added. 30 min. $\times$ 350.

(e) Smears of experimental tube: S-180 cell counting = $5 \times 10^6$/ml, 1 mg of CHML-Y solution is added. 40 min. $\times$ 350.

(f) Smears of experimental tube: S-180 cell counting = $5 \times 10^6$/ml, 1 mg of CHML-Y solution is -added 50 min. $\times$ 350.

(g) Smear of control tube: S-180 cell counting = $5 \times 10^6$/ml, no CHML-Y solution is added, 50 min. $\times$ 350.

All of the S-180 sarcoma cells are attacked, and turned to fragments.

Figure 4:
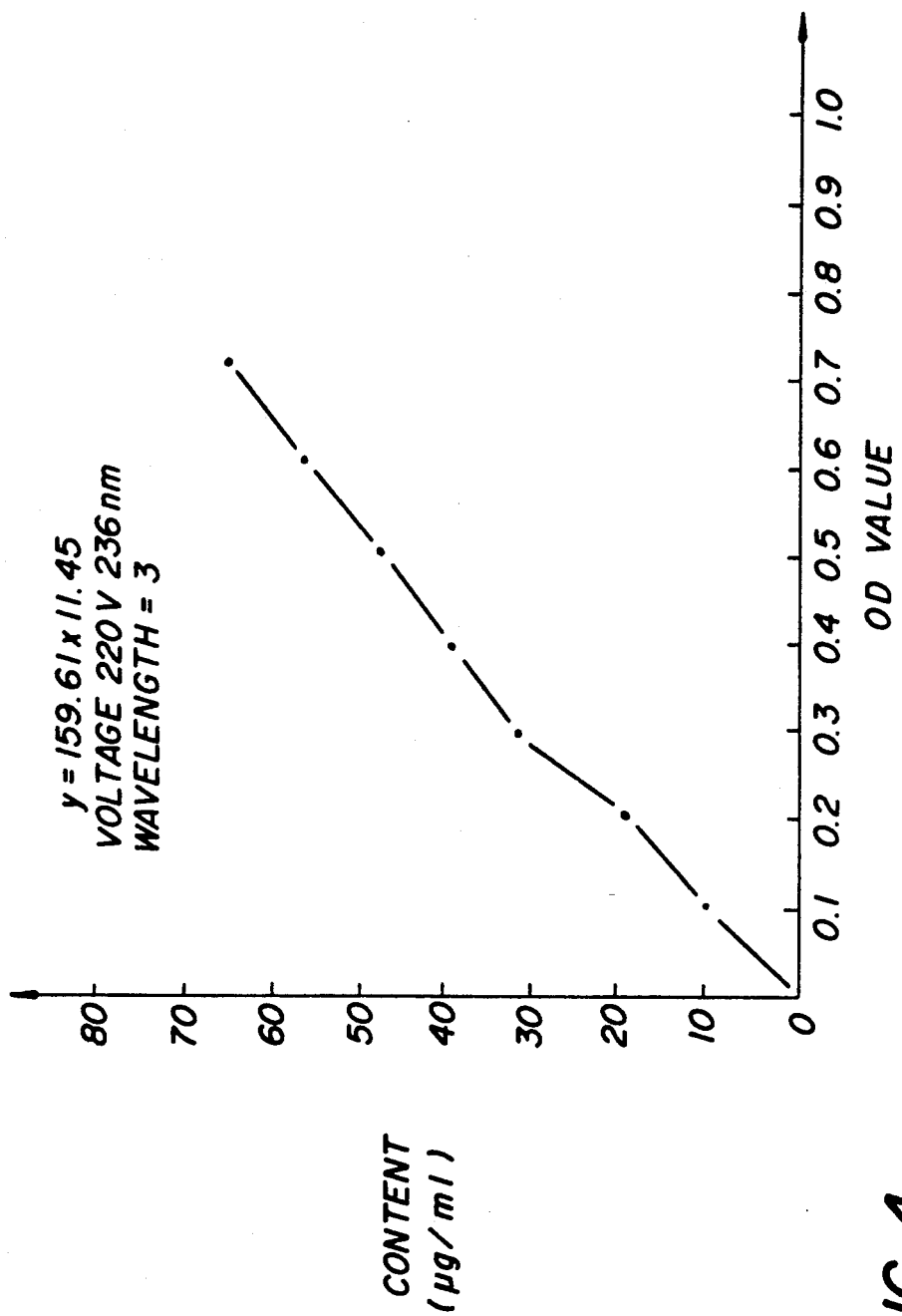

FIG. 4 The standard curve of CHML-M standard reagent, designed by this invention.

DETAILED DESCRIPTION OF THE INVENTION

Upon investigation, it has been found by the inventor that the molecular structure of the liposomes of the prior art can be described as a "stick", in which the handle is the hydrophilic radical of phosphatide in combination with cholesterol, while the straight rod portion of the stick is the place where the molecule of phosphatide and the like are located. Phosphatide consists of phosphoric acid and fatty acids and with the gathering of those sticklike molecules, liposomes of multilayer cyst structure, which is both hydrophilic and lipophilic, forms. It appears to be an irregular spherical particle under the microscope, the diameter of which is approximately 5 um.

Through a lot of experiments, a series of "molecular lipids", have been prepared by the inventor. The molecular lipids may be deemed to be a segment of the straight rod of the stick, namely, it comprises only the fatty acid part of the liposome, getting rid of both handle and phosphoric acid part. Thus, a series of "molecular lipids" having significant therapeutic effects has been obtained, which need not gather together to form a relatively large "body" of particle multilayers, and each molecule of which is an element particle of the "lipids" with polar and non-polar groups to carry pharmaceutical. The molecular lipids of the invention are of the following molecular formulae I–IV, except squalene:

$$R^1-\overset{O}{\underset{\|}{C}}-A; \qquad (I)$$

$$R^2-\overset{O}{\underset{\|}{C}}-A; \qquad (II)$$

$$R^3-\overset{O}{\underset{\|}{C}}-A^1; \qquad (III)$$

$$R^4-CH_2-A^1 \qquad (IV)$$

wherein $R^1$ is a $C_{12}$–$C_{20}$ saturated fatty acid radical; $R^2$ is a $C_{16}$–$C_{30}$ unsaturated fatty acid radical; $R^3$ is a prostaglandin radical; $R^4$ is a liposoluble vitamin radical; A is —OX or —X; $A^1$ is —$OX^1$ or —$X^1$; X is a positive ion selected from the group consisting of: Pt, Cu, Zn, Co, Mg, Ca, K and Na, or a negative ion selected from the group consisting of Cl, F, Br, I, N, Se, or a molecular radical selected from the group consisting of an alcohol radical, a phenol radical, an ether radical, an aldehyde radical, a keto radical, a quinoid radical, a pyrimidine radical, a purine radical, an amino acid radical and a gluclose radical; and $X^1$ is X or H. X, $X^1$, OX and $OX^1$ are hydrophilic radicals and $R^1$–$R^4$ are lipophilic radicals.

"A" and "$A^1$" are X and $X^1$, for example, when the respective starting materials are reacted with uracil or 6-mercaptopurine.

Being a molecular carrier, there is a part in the molecular structure of the molecular lipids which is able to bind a molecule of anticancer drugs. The drugs may be bound to the hydrophilic protion or the lipophilic portion. The anticancer drug molecule can also be bound as the X or $X^1$ moiety.

The hydrophilic radical of the molecule of lipids comes into contact with the surface of the outer membrane of the cell first, while the molecule is self rotating, and then spirally turning for 180° so as for the hydrophobic radical of the molecule to enter into the membrane interval. Consequently, the whole molecule gets into the membrane interval. Afterwards, the hydrophobic radical of the molecule of lipids comes into contact with the inner surface of the membrane interval, spirally turning for 180° once more, and then the hydrophilic radical goes beyond the inner surface of the membrane interval and comes into the cytoplasma of the cell. This is the mechanism for the molecular lipids of the invention to enter into the cell in turning 360°.

Most of the external lipids must be hydrolyzed into molecular lipids when they are to be absorbed by the biomembrane. The molecular lipids possess amphotericity of hydrophilic and lipophilic properties. The molecular lipids of the membrane of cells comprise various saturated fatty acids, unsaturated fatty acids, phosphoric acids, glycerine, cholesterol and liposoluble vitamins, etc. Separating the inner part of the cell from outside, these substances constitute the lipid osmotic pressure of the cell membranes. Under certain conditions, for example, under ultraviolet rays, the saturated and the unsaturated fatty acid, co-existing in the biomembrane, shall be interconvertable by means of dehydrogenation. The saturated fatty acid in the biomembrane increases the viscosity and stability of the biomembrane to enhance relatively the capillary circulation, while the unsaturated fatty acid in biomembrane increases the fluidity and instability of biomembrane to diminish relatively the capillary circulation. Conversely, when the saturated fatty acid in blood increases, the amount of blood in capillary circulation will be relatively diminished, and when the unsaturated fatty acid in blood increases, the amount of blood in capillary circulation will be relatively increased.

When the external lipids have just arrived the saturated concentration of lipids of cells in inside and outside dynamic balance, the attractive force to the lipids will disappear from the inside so that the molecular lipids shall not be able to enter into the inside of the cells. The magnitude of the osmotic pressure of the external molecular lipids has concern with the hydrophilic-lipophilic balance (HLB) of the biomembrane molecular lipids and with the external molecular lipids themselves. The osmotic ratio (osmotic coefficient) of the external molecular lipids is directly (positively) proportional to surface area, and inversely proportional in magnitude of the external molecular lipids. When a normal human is in a hungry state, the osmotic pressure of lipids within and without the cell is in dynamic balance, and the attractive force to the lipids will disappear. Consequently, the molecular lipids shall not be able to enter the cell. The infiltrate osmotic pressure in the state of dynamic balance averages about 0.127–0.318 atm. (96.52–241.47 mmHg). The external factors such as physical, chemical and biological factors shall first raise the lipids osmotic pressure owing to the change in osmotic pressure of the ions in the membrane, thus thinning out of the membrane structure with the traction. With the percolation of the cholesterol and the lipids, the biomembrane will be heavily damaged and the osmotic pressure of lipids will be diminished. Using molecular lipids which are originated from normal cells of animals and plants and are essential to human beings, the present invention has achieved the goal to control the osmotic pressure of lipids in abnormal cells or cancer cells and to effectively inhibit the growth, propagation and mitosis of abnormal cells and cancer cells. When they are carrying anti-cancer drugs, the molecular lipids provided by the present invention shall provide more strong synergistic effects.

For more than ten years researching and experimenting, the inventor has successfully discovered and prepared a series of molecular lipids to achieve the objects put forth in the present invention, which is named by the inventor "CHML" in the abbreviation of "Cytotropic Heterogeneous Molecular Lipids".

C, Cytotropic, means that the lipids have an affinity for cytological cells. Owing to that the substances of the lipids are extracted from biological cells, or, the biological cells comprise the substances of the lipids, the substances of the lipids are of affinity for the membrane structure of any living cells, especially for the membrane structure of abnormal cells. At the same time, the lipids possess the effect of stimulation of immunocytes, particularly of B-immunocytes and phagocytes (of mononuclear phagocyte system) to produce immunity reaction. Thus, CHML shall possess the ability of activating immunocytes to serve the function of immunity.

H, Heterogeneous, means that the lipids have the properties in physics, chemistry and biology which are similar to those of a biomembrane. Especially, the lipids possess the properties for idiosyncratic absorption to the abnormal membrane structure, while they are capable of compatibility with water solution of polar molecules or water-soluble drugs as well as with liposoluble substances. Sometimes even molecules of gases can be dissolved in the lipids. On the other hand, H stands for the fact that the attractive forces between the atoms exerted by the atoms of the elements in the molecule structure of the lipids are not equal, since there is positive-negative weak electrode at the both ends of the molecule; thus the lipids per se, are of heterogeneity.

Figure 1:
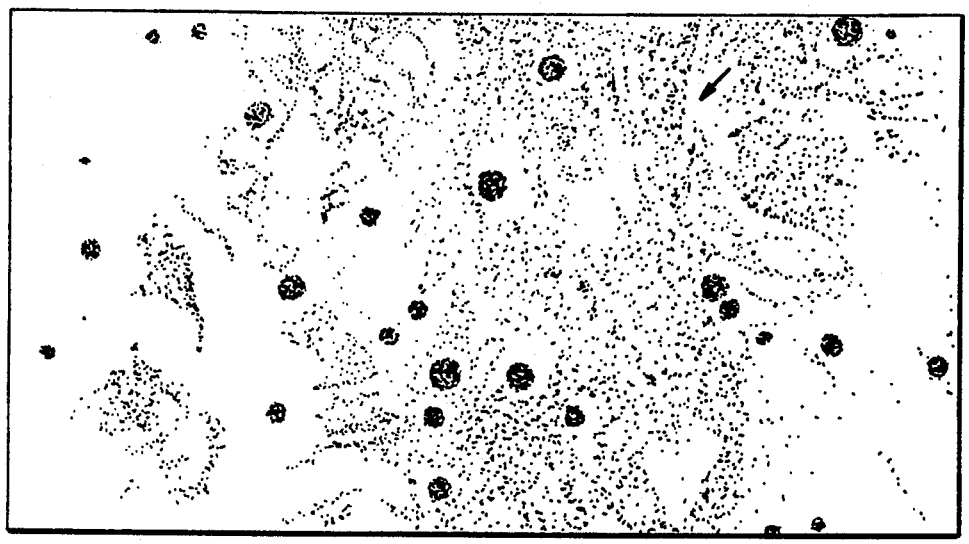
FIG. 1 photograph of transmission electron microscope, (JEM 200 CX, 100 kv.) it shows the molecular size of CHML, CHML-Y type molecule is shown by the arrow head. Amplification: 525000 times.
Figure 2:
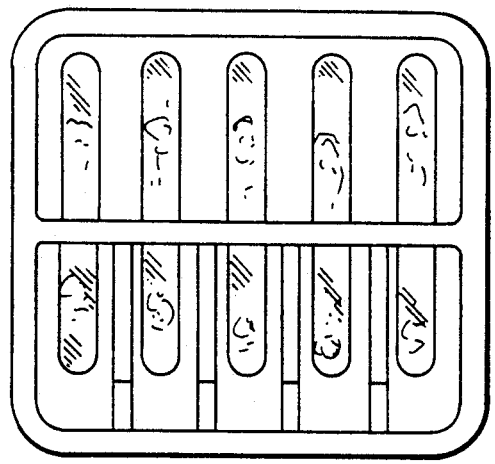
FIG. 2 photograph of CHML-Y product, CHML-Y is a transparent liquid, this product has been stored for 2 years.
Figure 3A:
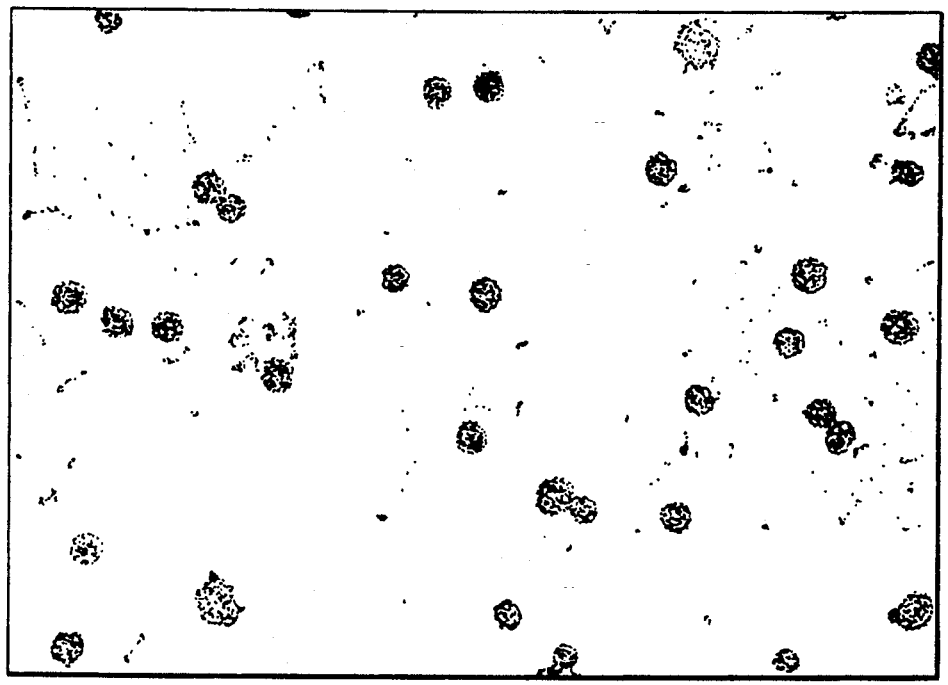
FIG. 3 photographs for the anti-S-180 sarcoma cell test.
Figure 3B:
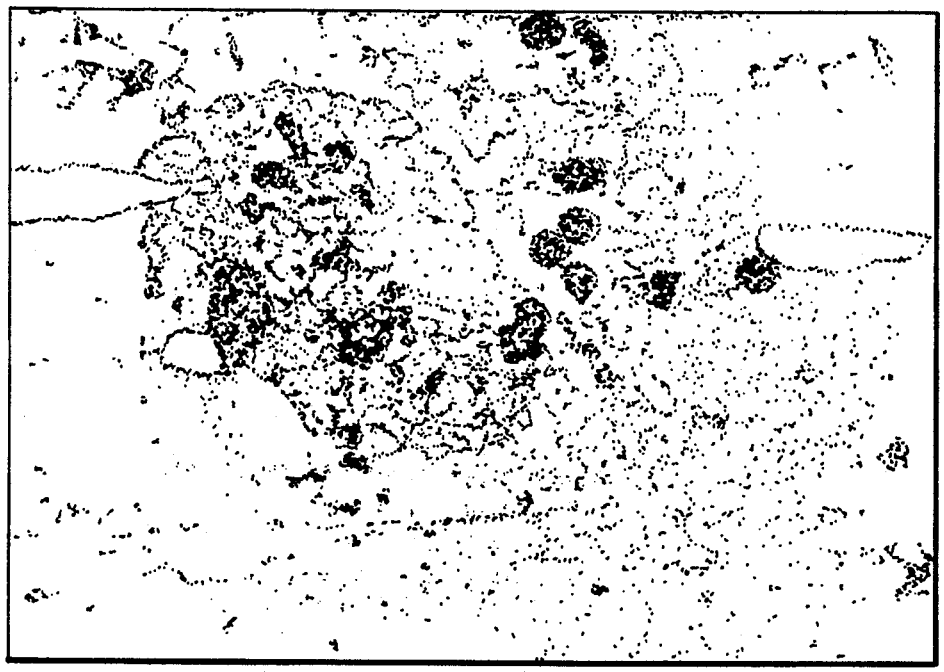
Figure 3C:
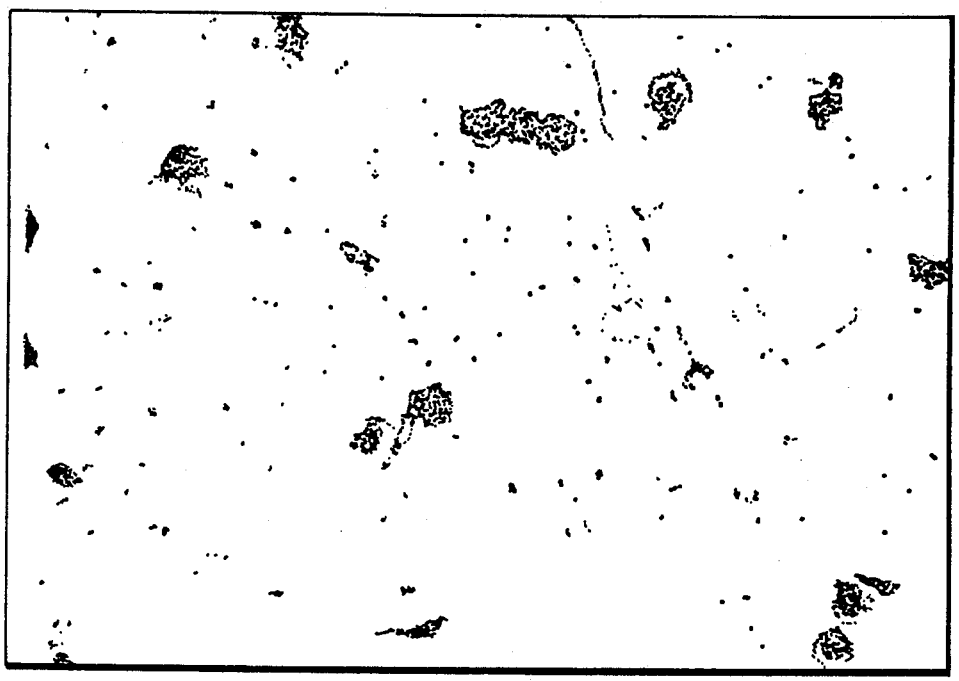
Figure 3D:
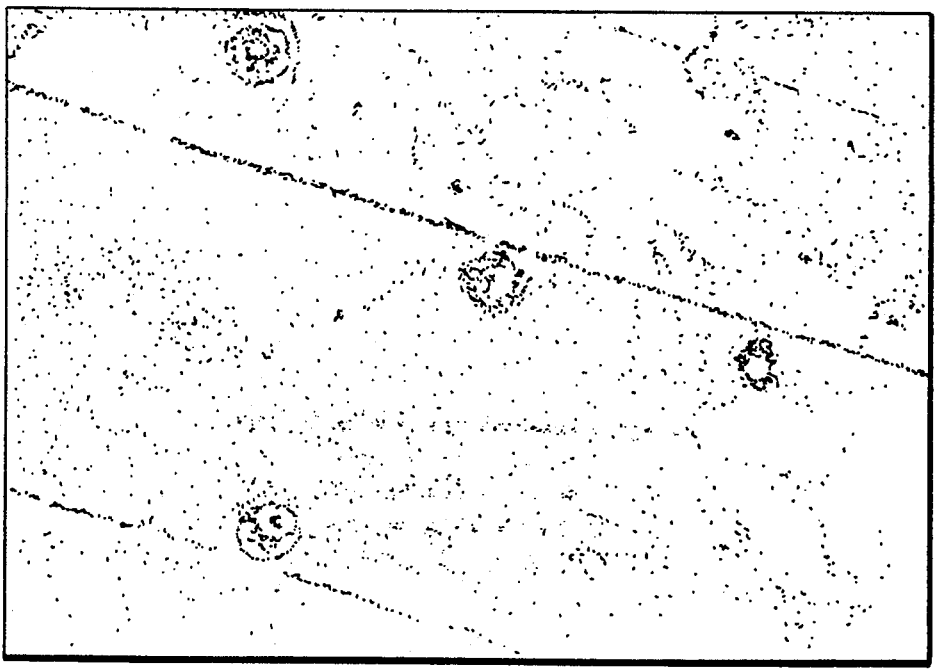
Figure 3E:
Figure 3F:
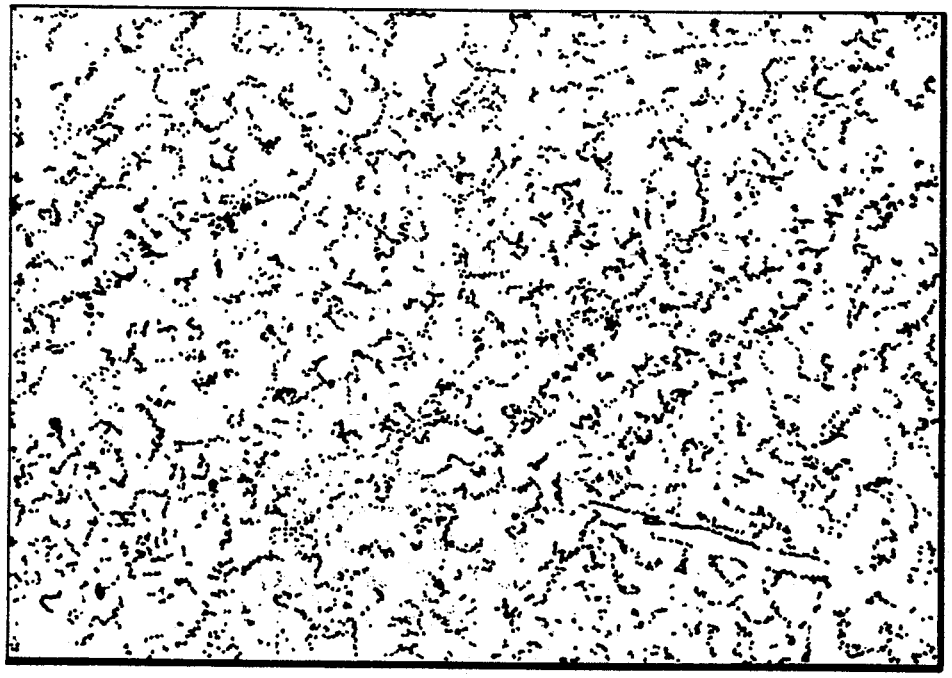
Figure 3G:
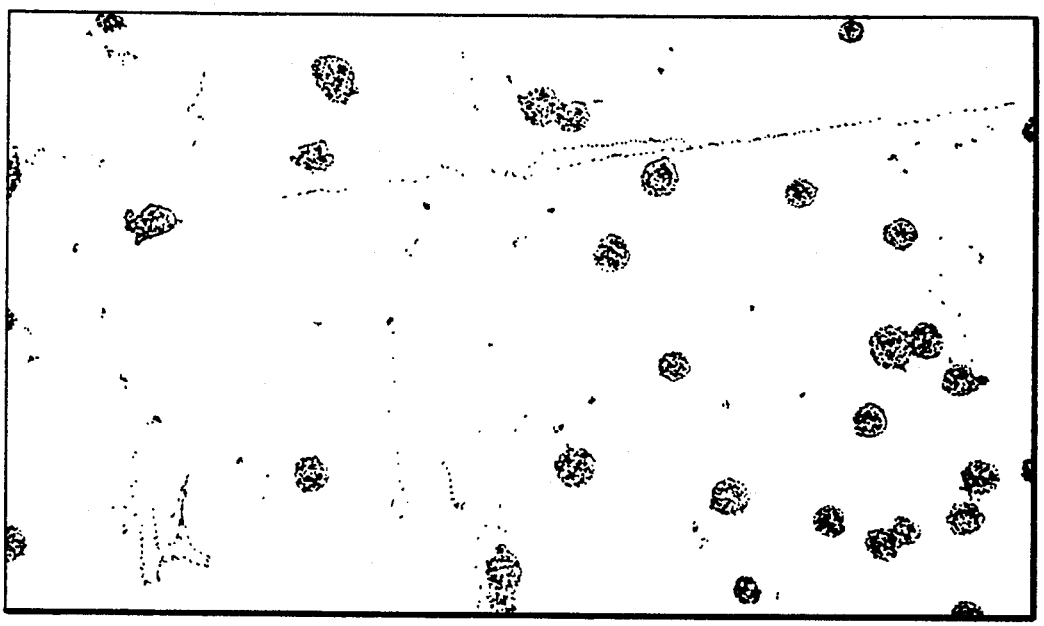

M, Molecular, means that the lipids are of molecular size, having average molecular weight of about 300 and dimensions of about $(20-30) \times (8-10) \times (4-6)$ Å (FIG. 1), being less than 1/10 of the size of a liposome of the prior art. The lipids exist as a transparent clear liquor (it can be explained by Tyndall effect).

L, Lipids, means that the molecular composition structure and therapeutic effects of the carrier provided by the invention are quite different from that of the liposomes of the prior art, and are novel and unique.

The molecular structure of CHML is relatively small so that it can easily penetrate into the biomembrane of the target abnormal cells to enter into the target cells. In contrast, a liposome or a polyphase liposome enters into the cells mainly in dependence on phagocytosis of the cells.

Playing the significant role of a carrier as a "bimolecular missile", CHML of the invention is able to strongly kill the cancer cells as well. Abnormal metabolism of the lipid substances in cancer cells has been discovered. The experiments in vitro have shown that CHML is able to destroy S180 sarcoma cells within 50 minutes (FIG. 3).

As a molecular carrier, CHML gives full play to carrying not only the hydrophilic and lipophilic molecules of pharmaceuticals, but also gas-carrying drugs, into the target cells. Simultaneously, CHML has the compatibility with more than two phases of drugs to carry into therapeutic effects, while a liposome or a polyphase liposome of the prior art is seldom reported in this respect.

CHML of this invention functions in promoting immunity of the cells, particulary B-lymphocytes, of human beings.

CHML of the invention is substantially extracted from cells of natural organisms. In other words, the cells of natural organisms contain the components of CHML of this invention. CHML provides little harmful side effects to human beings, and possesses good room temperature stability so that they may be kept in storage for more than two years at atmospheric pressure without deterioration of its properties. CHML of this invention does not contain phosphatide and the additives such as PVP (polyvinylpyrrolidone) and the like, while it tends to diminish the toxicity and side-effects of the drugs carried.

The CHML of the invention will be of great value to the wide application in medical science and other fields. Particularly, CHML of the invention has the function of antihypertension and of obvious inhibition on various viruses.

The compositions of CHML of this invention are prepared substantially from saturated fatty-acids, unsaturated fatty-acids, liposoluble vitamins and prostaglandin, which can be selected from the substances listed in Table 1.

TABLE 1

(1) Dodecane acid (lauric acid)
$CH_3(CH_2)_{10}COOH$
$C_{12}H_{24}O_2 = 200$ (2) Tetradecanoic acid (myristic acid)
$CH_3(CH_2)_{12}COOH$
$C_{14}H_{28}O_2 = 228$ (3) Palmitic acid
$CH_3(CH_2)_{14}COOH$
$C_{16}H_{32}O_2 = 256$ (4) Stearic acid
$CH_3(CH_2)_{16}COOH$
$C_{18}H_{36}O_2 = 284$ (5) Eicosanoic acid
$CH_3(CH_2)_{18}COOH$
$C_{20}H_{40}O_2 = 312$ (6) Palmitoleic acid (mainly Δ9-hexadecenoic acid)
$CH_3(CH_2)_5CH=CH(CH_2)_7COOH$
$C_{16}H_{30}O_2 = 254$ (7) Oleic acid (mainly Δ-9 octadecenoic acid)
$CH_3(CH_2)_7CH=CH(CH_2)_7COOH$
$C_{18}H_{34}O_2 = 282$ (8) Linoleic acid (mainly Δ9-12 octadecadienoic acid)
$CH_3(CH_2)_4CH=CHCH_2CH=CH(CH_2)_7COOH$
$C_{18}H_{32}O_2 = 280$ (9) Linolenic acid (mainly Δ9, 12, 15 octadecatrienoic acid)
$CH_3(CH_2)CH=CHCH_2CH=CHCH_2CH=CH(CH_2)_7COOH$
$C_{18}H_{30}O_2 = 278$

(10) τ-linolenic acid (mainly Δ6, 9, 12 octadecatrienoic acid)
$CH_3CH_2CH_2CH_2CH_2CH=CHCH_2CH=CHCH_2CH=CH(CH_2)_4COOH$
$CH_{18}H_{30}O_2 = 278$

TABLE 1-continued

(11) Eicosatetraenoic acid (mainly Δ5, 8, 11, 14 eicosatetraenoic acid)
$CH_3(CH_2)_4CH=CHCH_2CH=CHCH_2CH=CHCH_2CH=CH(CH_2)_3COOH$
$C_{20}H_{32}O_2 = 304$

(12) Eicosapentaenoic acid (mainly EPA)
$CH_3CH_2CH=CHCH_2CH=CHCH_2CH=CHCH_2CH=CHCH_2CH=CHCH_2$
$CH_2CH_2COOH$
$C_{20}H_{30}O_2 = 302$

(13) Docosahexenoic acid (mainly DHA)
$CH_3CH_2CH=CHCH_2CH=CHCH_2CH=CHCH_2CH=CHCH_2CH=CHCH_2$
$CH=CHCH_2CH_2COOH$
$C_{22}H_{32}O_2 = 328$

(14) Eicosenoic acid (mainly Δ10 - eicosenoic acid)
$CH_3(CH_2)_8CH=CH(CH_2)_8COOH$
$C_{20}H_{38}O_2 = 310$

(15) Eicosadienoic acid (mainly Δ9, 12-eicosadienoic acid)
$CH_3(CH_2)_6CH=CH(CH_2)CH=CH(CH_2)_7COOH$
$C_{20}H_{36}O_2 = 308$

(16) Eicosatrienoic acid (mainly Δ9, 14, 17-eicosatrienoic acid
Δ8, 11, 14-eicosatrienoic acid)
$CH_3(CH_2)_3CH=CHCH_2CH=CHCH_2CH=CH(Ch_2)_7COOH$
$CH_3(CH_2)_4CH=CHCH_2CH=CHCH_2CH=CH(CH_2)_6COOH$
$C_{20}H_{34}O_2 = 306$

(17) Docosadienoic acid (mainly Δ9.11-docosadienoic acid)
$CH_3(CH_2)_8CH=CHCH_2CH=CH(CH_2)_7COOH$
$C_{22}H_{40}O_2 = 336$

(18) Doconsenoic acid (mainly Δ11-docosenoic acid)
$CH_3(CH_2)_9CH=CH(CH_2)_9COOH$
$C_{22}H_{42}O_2 = 338$

(19) Docosatrienoic acid (mainly Δ9, 12, 15-docosatrienoic acid
Δ8, 11, 14-docosatrienoic acid)
$CH_3(CH_2)_5CH=CHCH_2CH=CHCH_2CH=CH(CH_2)_7COOH$
$CH_3(CH_2)_6CH=CHCHCH=CHCHCH=CH(CH_2)_6COOH$
$C_{22}H_{38}O_2 = 334$

(20) Docosatetraenoic acid (mainly Δ7, 10, 13, 16 - docosatetraenoic acid
Δ6, 9, 12, 15 - docosatetraenoic acid)
$CH_3(CH_2)_4CH=CHCH_2CH=CHCH_2CH=CHCH_2CH=CH(CH_2)_5COOH$
$CH_3(CH_2)_5CH=CHCH_2CH=CHCH_2CH=CHCH_2CH=CH(CH_2)_4COOH$
$C_{22}H_{36}O_2 = 332$

(21) Docosapentaenoic acid (mainly Δ5, 8, 11, 14, 17-docosapentaenoic acid)
$CH_3(CH_2)_4CH=CHCH_2CH=CHCH_2CH=CHCH_2CH=CHCH_2CH=CH(CH_2)_3COOH$
$C_{22}H_{34}O_2 = 330$

(22) Tetracosenoic acid (mainly Δ12-tetracosenoic acid)
$CH_3(CH_2)_{10}CH=CH(CH_2)_{10}COOH$
$C_{24}H_{46}O_2 = 366$

(23) Tetracosandienoic acid (mainly Δ10, 13-tetracosandienoic acid
11, 14-tetracosandienoic acid)
$CH_3(CH_2)_9CH=CHCH_2CH=CH(CH_2)_8COOH$
$CH_3(CH_2)_8CH=CHCH_2CH=CH(CH_2)_9COOH$
$C_{24}H_{44}O_2 = 364$

(24) Tetracosantrienoic acid (mainly Δ9, 12, 15-tetracosantrienoic acid)
$CH_3(CH_2)_7CH=CHCH_2CH=CHCH_2CH=CH(CH_2)_7COOH$
$C_{24}H_{42}O_2 = 362$

(25) Tetracosantetraenoic acid (mainly Δ7, 10, 13, 16-tetracosantetraenoic acid)
$CH_3(CH_2)_6CH=CHCH_2CH=CHCH_2CH=CHCH_2CH=CH(CH_2)_5COOH$
$C_{24}H_{40}O_2 = 360$

(26) Tetracosanpentaenoic acid (mainly Δ6, 9, 12, 15, 18-tetracosanpentaenoic acid)
$CH_3(CH_2)_4CH=CHCH_2CH=CHCH_2CH=CHCH_2CH=CHCH_2CH=CH(CH_2)_4COOH$
$C_{24}H_{38}O_2 = 358$

(27) Tetracosanhexenoic acid (mainly Δ6, 9, 12, 15, 18, 21-tetracosanhexenoic acid)
$CH_3(CH_2)CH=CHCH_2CH=CHCH_2CH=CHCH_2CH=CHCH_2CH=CHCH_2CH=CH(CH_2)_4COOH$
$C_{24}H_{36}O_2 = 356$

(28) Squalene (mainly Δ2, 6, 10, 14, 19, 22 traicohexaenoic acid)

TABLE 1-continued

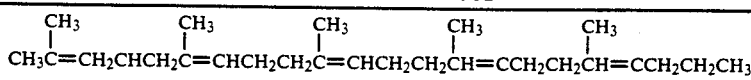
CH=CCH₃
$C_{30}H_{50} = 410$

(29) Vitamin A

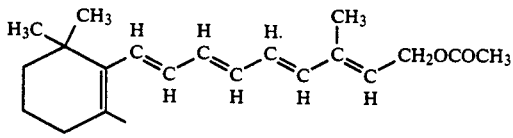

$C_{22}H_{32}O_2 = 328$

(30) Vitamin D

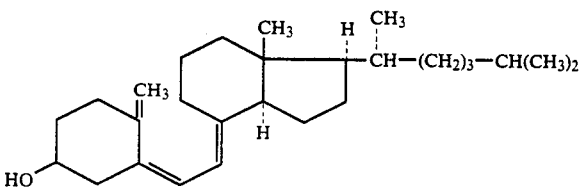

$C_{27}H_{44}O = 384$

(31) Vitamin E

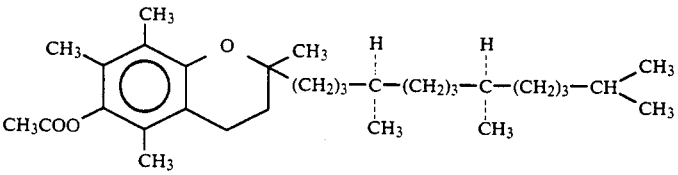

$C_{31}H_{52}O_3 = 472$

(32) Prostaglandin

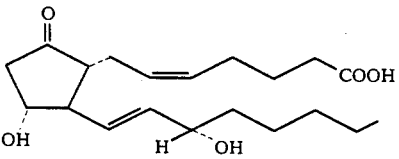

$C_{20}H_{32}O_5 = 352$

Any one selected from the substances listed in Table 1 can be used to prepare the CHML of the invention by substituting H with X or X¹ (for squalene, prostaglandin and Vitamins A, D and E, the said substitution may not be necessary), expressed by the structural formulae I-IV as follows:

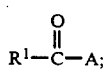 (I)

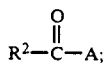 (II)

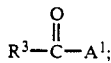 (III)

R⁴—CH₂—A¹ (IV)

wherein R¹-R⁴, A, A¹, X and X¹ are as defined above.

The compositions of CHML are substantially extracted from the cells of animals and plants and may be obtained by any laboratory or industrial method. No matter how they are available, the substances selected need to be determined by qualitative and quantitative analysis prior to use, to satisfy the requirements of various compositions provided. There are proper methods for the compositions of the molecular lipids to be determined in qualitative and quantitative analysis, such as the application of fatty acid sequence analysis by elevated temperature gas chromatographic technique, conventional gas chromatography, Iodine value determination ultraviolet spectrometry, AgNC TLC, and others such as Mass spectrography, NMR, X-RAY diffraction IR and laser spectroscopy for qualitative and quantitative determination of molecular lipids specifically. Using Nitrogen Molecule Laser in Laser chromatography is preferred, the determination of qualitative and quantitative microanalysises results in quick and accurate effects.

After being determined of their molecular structures and contents, the various compositions are then purified by means of molecular ultrafiltration and/or molecular-recrystallization, and then formulated in accurate weight and by heterogeneous rearrangement in accordance with the composition of CHML of the invention, and mixed thoroughly at a temperature about 303°-353° K. for about 10-30 minutes. After reducing the temperature to about 288°-298° K. the mixture is passed through sintered glass filter to obtain the filtrate as a clear and transparent liquid of the CHML of the invention.

Generally, the pharmaceutical compositions of the present invention comprise:

(1) 3-30 parts by weight of saturated fatty acid derivatives with the general formula:

(2) 50-90 parts by weight of unsaturated fatty acid derivatives with the general formula:

(3) 0-0.2 parts by weight of prostaglandin or derivatives thereof, with the general formula:

(4) 0.2-10 parts by weight of liposoluble vitamins or derivatives thereof, with the general formula:

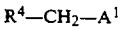

wherein $R^1$ is a $C_{12}-C_{20}$ saturated fatty acid radical; $R^2$ is a $C_{16}-C_{30}$ unsaturated fatty acid radical; R3 is prostaglandin radical; $R^4$ is a liposoluble vitamin radical; A is —OX or —X; $A^1$ is —OX$^1$ or —X$^1$; X is a positive ion selected from the group consisting of Pt, Cu, Zn, Co, Mg, Ca, K, Na; a negative ion selected from the group consisting of Cl, F, Br, I, N, Se; a molecular radical selected from the group consisting of an alcohol radical, a phenol radical, an ether radical, an aldehyde radical, a keto radical, a quinoid radical, a pyrimidine radical, a purine radical, an amino acid radical and a glucose radical; and $X^1$ is X or H.

Generally, the preferred pharmaceutical compositions of the present invention comprise:

(1) 5-20 parts by weight of saturated fatty acid derivative with the general formula:

(2) 66-85 parts by weight of unsaturated fatty acid derivatives with the general formula:

(3) 0.01-0.2 parts by weight of prostaglandin or derivatives thereof, with the general formula:

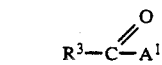

(4) 0.3-8 parts by weight of liposoluble vitamins or derivatives thereof, with the general formula:

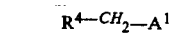

wherein $R^1$ is a $C_{12}-C_{20}$ saturated fatty acid radical, preferably selected from the group consisting of a dodecanoic acid (lauric acid) radical, a tetradecanoic acid (myristic acid) radical, a palmitic acid radical, a stearic acid radical and an eicosanoic acid radical, and more preferably selected from the group consisting of a stearic acid radical and a palmitic acid radical; $R^2$ is a $C_{16}-C_{30}$ unsaturated fatty acid radical, preferably selected from the group consisting of a palmitoleic acid radical, an oleic acid radical, a linoleic acid radical, an τ-linolenic acid radical, a linolenic acid radical, an eicosatetraenoic acid radical, an eicosapantaenoic acid radical, a dodosahexenoic acid radical, an eicosenoic acid radical, a docosenoic acid radical, a docosadienoic acid radical, a docosatrienoic acid radical, a docosatetraenoic acid radical, a docosapentaenoic acid radical, a tetracosenoic acid radical, a tetracosandienoic acid radical, a tetracosantrienoic acid radical, a tetracosantetraenoic acid radical, a tetracosanpentaenoic acid radical, a tetracosanhexenoic acid radical and a squalene radical, and more preferably selected from the group consisting of an τ-linolenic acid radical, an oleic acid radical, an eicosatetraenoic acid radical, an eicosapentaenoic acid radical, an eicosatrienoic acid radical, a docosahexenoic, acid radical, a tetrocosenoic acid and squalene; $R^3$ is a prostaglandin radical; $R^4$ is selected from the group consisting of a Vitamin A radical, a Vitamin D radical and a Vitamin E radical; A is —OX or —X; $A^1$ is —OX$^1$ or X$^1$; X is a positive ion selected from the group consisting of Pt, Cu, Zn, Co, Mg, Ca, K and Na, a negative ion selected from the group consisting of Cl, F, Br, I, N, Se, a molecular radical selected from the group consisting of an alcohol radical, a phenol radical, an ether radical, an aldehyde radical, a keto radical, a quinoid radical, a pyrimidine radical, a purine radical, an amino acid radical and a glucose radical; and $X^1$ is X or H. Preferably, X and $X^1$ are a pyrimidine radical, a purine radical, F, Mg, Ca, K or Na, respectively; more preferably X and $X^1$ are a pyrimidine radical, a purine radical or F, respectively. The above-mentioned saturated fatty acid derivatives preferably comprise at least one member selected from the group consisting of $C_{12}-C_{20}$ saturated fatty acid derivatives; said unsaturated fatty acid derivatives preferably comprise at least one member selected from the group consisting of $C_{16}-C_{30}$ unsaturated fatty acid derivatives; and liposoluble vitamin derivatives preferably comprise at least one member selected from the group consisting of a Vitamin A derivative, a Vitamin D derivative and a Vitamin E derivative.

A specific example of composition of CHML is wherein:

(1) The saturated fatty acid derivatives comprise:
6.5-12 parts by weight of a palmitic acid derivative;
5-10 parts by weight of a stearic acid derivative;
(2) The unsaturated fatty acid derivatives comprise:

0.5-2 parts by weight of a squalene derivative;
0.7-2.5 parts by weight of a τ-linolenic acid derivative;
1-4 parts by weight of a linolenic acid derivative;
14-28 parts by weight of an oleic acid derivative;
3-7 parts by weight of an eicosatetraenoic acid derivative;
8-11 parts by weight of an eicosapentaenoic acid derivative;
2-4 parts by weight of a eicosatrienoic acid derivative;
10-15 parts by weight of a docosahexenoic acid derivative;
2-4 parts by weight of a tetrocosenoic acid derivative;
4-6 parts by weight of a docosenoic acid derivative;
0.5-2 parts by weight of a docosadienoic acid derivative;
1-3 parts by weight of a docosatrienoic acid derivative;
3-7 parts by weight of a docosatetraenoic acid derivative;
5-10 parts by weight of a docosapentaenoic acid derivative;
10-20 parts by weight of a palmitoleic acid derivative;

(3) The liposoluble vitamins or derivatives thereof comprise:
0-0.5 parts by weight of Vitamin A or derivatives thereof;
0-0 5 parts by weight of Vitamin D or derivatives thereof;
3-7 parts by weight of Vitamin E or derivatives thereof; and X and $X^1$ in above-mentioned derivatives is pyrimidine radical, purine radical, F, Ca or Na, respectively.

The composition mentioned above can be used for treating cancer, such as small cell lung cancer, sarcoma-180, Lewis lung carcinoma, human lung carcinoma, HeLa cancer cell, melanoma, granuloma fungoides (T cell tumor), squamous carcinoma and pigmentary basaloma, among others.

As a result of a large amount of experiments, a series of prescribed-compositions of CHML has also been developed by the inventor which possess various essential effects besides those of liposome carriers in the prior art. In principle, only at least one substance selected from the group consisting of saturated fatty-acid derivatives, unsaturated fatty-acid derivatives, and liposoluble vitamins or derivatives, and prostaglandin or derivatives are sufficient for constituting the CHML of the invention. In order to make CHML having more functions and effects, it is preferably desired to increase one or more components in accordance with the requirements of functions and therapeutic effects, for example:

CHML-Y form possesses synergistic anti-cancer effects,

CHML-V form possesses synergistic cancer-prophylactic effects,

CHML-A form possesses the synergistic effects of induction and enhancement of the immunity function of B-cell and leucocyte, CHML-M form possesses the function of monitoring membrane structure of cells, CHML-C form possesses the synergistic antivirus effects CHML-H form possesses the synergistic effects of anti hypertension and anti-angiosclerosis CHML-O form is a carrier type of molecular lipids In principle, at least only one component substance selected from the group consisting of saturated and unsaturated fatty acids, or one kind of liposoluble vitamin or prostaglandin listed in Table 1 may constitute the raw materials of molecular lipids of CHML. It is preferable that one or more other component substances selected from Table 1 should be blended to make the functions and effects perfect of the CHML. Thus, a series of prescribed compositions of CHML are provided in the invention such as above-styled forms of Y through O. In theory, lots of compositions can be constituted by combination of 2 to 32 substances listed in Table 1. Thus, rational selection and compatibility are required in accordance with the practical functions and effects. Therefore, the prescription-compositions of the raw materials of the above-styled forms of CHML provided in the invention are listed to illustrate with examples as follows:

EXAMPLE 1

| CHML-Y | |
|---|---|
| Squalene | 0.5-2.0 wt. % |
| τ-linolenic acid | 0.7-2.5 wt. % |
| Linolenic acid | 1.0-4.0 wt. % |
| Oleic acid | 14-28 wt. % |
| Stearic acid | 5-10 wt. % |
| Palmitic acid | 6.5-12 wt. % |
| Eicosatetraenoic acid* | 3-7 wt. % |
| Eicosapentaenoic acid* | 8-11 wt. % |
| Eicosatrienoic acid* | 2-4 wt. % |
| Docosahexenoic acid | 10-15 wt. % |
| Tetrocosenoic acid* | 2-4 wt. % |
| Vit E | 3-7 wt. % |
| Vit A | 0-0.5 wt. % |
| Vit D | 0-0.5 wt. % |
| Docosenoic acid | 4-6 wt. % |
| Docosadienoic acid | 0.5-2 wt. % |
| Docosatrienoic acid | 1-3 wt. % |
| Docosatetraenoic acid | 3-7 wt. % |
| Docosapentaenoic acid | 5-10 wt. % |
| Palmitoleic acid | 10-20 wt. % |

EXAMPLE 2

| CHML-V | |
|---|---|
| Vit A | 8-14 Wt. % |
| Vit D | 2-6 Wt. % |
| Vit E | 10-22 Wt. % |
| τ-linolenic acid | 0.5-8 Wt. % |
| Linoleic acid | 4-14 Wt. % |
| Oleic acid | 4-7 Wt. % |
| Palmitic acid | 13-19 Wt. % |
| Stearic acid | 7-14 Wt. % |
| Squalene* | 2-10 Wt. % |

EXAMPLE 3

| CHML-A | |
|---|---|
| Oleic acid | 19-30 wt. % |
| Linoleic acid | 0.5-2 wt. % |
| τ-Linolenic acid | 9-30 wt. % |
| Palmitic acid | 10-14 wt. % |
| Stearic acid | 4-6.5 wt. % |
| Vit D | 4-10 wt. % |
| Vit A | 0-4 wt. % |
| Vit E | 14.5-20 wt. % |
| Tetradecanoic acid | 0.5-4.5 wt. % |
| Prostaglandin F** | 0-0.2 wt. % |

EXAMPLE 4

| CHML-M | |
|---|---|
| Oleic acid | 18–26 wt. % |
| Linoleic acid | 3–12 wt. % |
| linolenic acid | 14–22 wt. % |
| Stearic acid | 10–18 wt. % |
| Palmitic acid | 15–24 wt. % |
| Eicosenoic acid* | 1.4–6 wt. % |
| Vit A | 0.5–1.5 wt. % |

EXAMPLE 5

| CHML-C | |
|---|---|
| Oleic acid | 25–28 wt. % |
| Linoleic acid | 1.5–4.5 wt. % |
| τ-linolenic acid | 25–28 wt. % |
| Palmitic acid | 14–16 wt. % |
| Tetracosantetraenoic acid* | 15–18 wt. % |
| Stearic acid | 8–10 wt. % |

EXAMPLE 6

| CHML-C | |
|---|---|
| Squalene* | 2.5–7.5 wt. % |
| Eicosapentaenoic acid | 15–20 wt. % |
| Eicosatetraenoic acid* | 8–12 wt. % |
| Eicosatrienoic acid* | 2–4 wt. % |
| τ-linolenic acid | 1–4 wt. % |
| Oleic acid | 5–10 wt. % |
| Linoleic acid | 1.5–3 wt. % |
| Stearic acid | 15–20 wt. % |
| Docosahexenoic acid | 2–25 wt. % |

EXAMPLE 7

| CHML-H | |
|---|---|
| Stearic acid | 5–10 wt. % |
| Linoleic acid | 10–18 wt. % |
| τ-linolenic acid | 4–10 wt. % |
| Oleic acid | 10–20 wt. % |
| Vit E | 5–12 wt. % |
| Vit A | 0.5–4 wt. % |
| Eicosapentaenoic acid* | 8–15 wt. % |
| Eicosatetraenoic acid* | 3–8 wt. % |
| Eicosatrienoic acid* | 4–10 wt. % |
| Palmitic acid | 6–8 wt. % |

EXAMPLE 8

| CHML-0-1 (hydrophilic type) | |
|---|---|
| Stearic acid | 10–19 wt. % |
| Palmitic acid | 12–20 wt. % |
| τ-linolenic acid | 24–34 wt. % |
| Oleic acid | 28–38 wt. % |

EXAMPLE 9

| CHML-0-2 (lipophilic type) | |
|---|---|
| Vit A | 1.5–4 wt. % |
| Vit D | 1.5–4 wt. % |
| Vit E | 14–18 wt. % |
| Oleic acid | 50–60 wt. % |
| Dodecanoic acid | 8–16 wt. % |

| -continued | |
|---|---|
| CHML-0-2 (lipophilic type) | |
| (lauric acid) | |
| Tetradecanoic acid | 5–12 wt. % |
| (myristic acid) | |

In examples 1 through 9, * means that the components may be treated with bio-molecular activation; ** means that the components may be treated with bio-molecular conversion, which will clearly described in the following examples.

It can be seen that the combination of hydrophilic molecular lipids as described in Ex. 8 and lipophilic molecular lipids as described in Ex. 9 gives a molecular lipid which exhibits both hydrophilic and lipophilic properties. These components are also substantially contained as the substance in Ex. 1 to Ex. 7. In another words, one or more component substances selected from Table 1 may be added to the hydrophilic and the lipophilic compositions of the molecular lipids to constitute the specific CHML which possesses various functions and effects in need in this invention.

In processing the prescribed compositions, additives such as surfactants may be selected to add with effect of "heterogenous rearrangement" of the prescriptive compositions provided in the invention. The term "heterogeneous rearrangement" in this invention means that the prescriptive compositions are rearranged to the extent that the molecules of which should be arranged substantially into ordered orientation according to their polarities, and the polar radicals of the additives, such as the surfactants, metal ions or non-metal ions or other ions should come into combination with the molecular lipids such that the molecular lipids should be capable of affinity for the membrane structure of the abnormal cells and thus exhibit biological effect more significantly.

Additives, such as surfactants, may be selectively added including tween, span, and other substances as glycerin, ether, ethanol higher alcohol sulfate (R—O—SO$_3$NA), alkyl benzene sulfonate (R—C$_6$H$_4$—SO$_3$NA), cholate, alkylamino-acids (R—NH—CH—COOH), long chain alkyl quaternary ammonium salts, sodium lauryl sulphate, sulfated oils, polyoxyethylene fatty alcohol ether, polyoxyethylene alkylphenoxy ether, KOH, NaOH, Ca(OH)$_2$, KCl, NaCl, CaCl$_2$, FeCl$_3$, FeCl$_2$, ZnCl$_2$, MgCl$_2$, MgSO$_4$, KI, NH$_4$Cl, NaHCO$_3$, ZnSO$_4$, Zn$_3$(PO$_4$)$_2$, fluoroalkane, HCl, KBr, NaBr, KI and the radicals of molecules of alcohol-form, phenol-form, ether-form, aldehyde-form, and quinoid-form, and the radicals of amino acid, glucose, pyrimidine, purine and any combination of these, etc. The best preferable composition of the additives comprises 10–90% glycerin, ether and ethanol, 90–10% higher alcohol sulfate, KOH, NaOH, fluorocarbon compound such as FC-80 (perfluorobutyltetrahydrofuran), FDC polyfluoronaphthalene, FTpA (trifluorotripropyl amine), etc. More preferable composition of the surfactants comprises 70–30% (wt) span, tween, glycerine, and alcohol, with addition of 30–70% KOH, NaOH, hydrogenated caster oil, polyoxyethylene ether, ether and steapsin.

The steps for rearrangement of heterogenous molecular lipids can be illustrated by the following examples.

EXAMPLE 10

At least one kind of additive as listed above e.g. KOH 30% aq. solution can be selected solely. It is warmed with addition of at least of one kind of molecular lipid component selected from Table 1, e.g. oleic acid is selected solely, or 60% alcohol and 5% MgSO can be selected as additives also. Upon addition of molecular lipid solution, such as oleic acid, it is warmed and maintained at 283°-340° K. The hydrophilic and lipophilic balance (HLB) is controlled at 3-16, pH 2-12, for 10-120 min. under stirring, until its density is very uniform. The thoroughly mixed solution attains transparent features. It is very finely dispersed suspension in which its molecular arrangement is very neat, that is the heterogeneous molecular lipid product.

The formulated preparations of the above heterogeneous molecular lipids can be prepared. They are illustrated in the following examples.

EXAMPLE 11

The above selected additives such as surfactants are added to freshly sterile water (for injection) and warmed together to 283°-363° K. to dissolve the additives, above accurately weight formulated components are added drop wise to the mixture at the same temperature and stirred thoroughly. A suitable amount of injectional water is further added according to its desired concentration, mixed and stirred to become a transparent clear solution, the heterogeneous rearrangement is attained.

It is filtered through $0.025\mu$ filtering membrane, perfused and sealed into an ampule under vacuum or nitrogen atmosphere, sterilized at $373° \pm 1°$ K. with live steam for 30-60 min. stored in a cold place and protected from light and heat, ready for use.

EXAMPLE 12

For adaptation of preparation of higher dosage, the mixture in example 1 is further homogenized in a high speed emulsifier, the pumps of emulsifier runs at 54 L/hr, working pressure 2000-8000 psi. The hydrophilic and lipophilic ratio (HLB) is maintained at 4-18. When the solution is mixed uniformly, its temperature is decreased to 293°-303° K., filtered through $0.6\mu$ membrane 0.2-2% active carbon is added to the filtrate and heated to $373° \pm 1°$ K. boiling for 30-60 min, the temperature is decreased to 288°-303° K., filtered through $0.45\mu$ membrane, the filtrate is centrifuged by ultracentrifuge, at 8000-50,000 rpm, a=15000-60000, for 5-10 min., 5 finally, the centrifugate is further filtered through $0.025\mu$ membrane, to obtain a clear transparent CHML filtrate, i.e. the heterogeneous rearrangement is attained, perfused and sealed into an ampule under vacuum or nitrogen atmosphere, sterilized with live steam at $373° \pm 1°$ K. for 30-60 min. stored in protection of light and in cold place, ready for use.

The components and formulations of the cytotropic heterogeneous molecular lipid CHML are described as above. The components can be derived from cell of plants and animals.

The source of cells of plants are taken from corn, peanut seed, sunflower, cotton seed, soy bean, horse bean, vigna saicensis, garden pea, pheseolus radiatus, tea seed, mung bean castor seed, cocoa bean, sesame, olive, seeds of Chinese vegetable tallow, pumpkin seed, seed of sponge gourd, white gourd, pine seed, coconut, rape seed etc. as well as their stems and leaves. Source of animal cells are taken from chicken, duck, goose, sparrow, cow, sheep, horse, pig, dog, deer, rabbit, tortoise and turtles and from marine organisms such as clam, couch oyster, shark, whale, cod, etc. The membrane of eggs of hen, duck and goose also can be used.

The components used in CHML are highly contained in the liver, heart, brain, marrow, nerve and adrenal gland of animals.

The main source of various components contained in CHML of this invention may be obtained from plants, such as the fruit of corn, sunflower, sesame, peanut, rape seed, soy bean or may be obtained from marine organisms such as scabbard fishes, carcherhenidea spp such as blue shark and white shark. Gadus spp. such as cod, and the mammals such as whale and the like.

The animals and plants to be used must be selected for health, and carry no genetic disease. The animals must have a certain extent of immunity. The animal organs to be used such as liver, kidney, heart, lungs, spleen and brain must be picked in accordance with specific requirements. Various components of saturated and unsaturated molecular lipids can be extracted from these organs according to the conventional art. For example the plants are selected, washed, dried, and crushed into small sizes. They are then warm pressed to get the crude vegetable oil or extracted with extracting agent as ether acetone etc. the crude oil vegetable product can also be obtained.

The vegetable oil as above for edible or medical use can be obtained from the market also. They can be used after their contents are determined. Other examples are: the corresponding animal tissue can be picked from animals under aseptic conditions and stored in 253° K. refrigerator or the fresh tissue may be directly used.

The tissue of the animals is subjected to a process for removal of impurities, crushed to small sizes, warmed at 303°-323° K. for 45 min. then centrifuged under 2000 rpm for 10-20 min. The residue is warmed in distilled water (30% of original tissue wt.), kept at such a temperature for 20 min, further centrifuged under 2000 rpm for 10-30 min, the supernatant is discarded, distilled water (80% of original tissue weight) is added with stirring, the animal oil is separated by means of a separating funnel, that is the crude animal lipid.

When the crude lipid is extracted from vegetables and animals, various techniques such as saponification, refrigerated centrifugation, or adsorption may be applied to separate the saturated and unsaturated fatty acids.

EXAMPLE 13

The vegetable oil is subjected to saponifications, the saponified liquor is maintained at 323 K, then is acidified with 1:1 (V/V) HCl solution to pH 3.0, settled, the aqueous layer is discarded, the oily layer is collected and the emulsified layer is extracted with ethyl ether, combined the oil layer and ether extract, evaporating off ether, 10 fold amount acetone solution is added to dissolve the remainder of the mixture. It is further subjected to fractional refrigeration according to their different freezing point of saturated fatty acid. It is freezed about 2 hrs., refrigerated centrifuged at 600-2000 rpm, for 5-10 min after the collection of various saturated fatty acids, evaporating off acetone, the mixed unsaturated fatty acids can be obtained.

EXAMPLE 14

3 fold amount of 95% ethyl alcohol is added to the homogenenated suspension of shark liver, the suspension is then filtered. The residue is further extracted with 2 fold amount of 95% ethanol, and filtered, the filtrate is combined and concentrated to remove alcohol.

Suitable amount of ethyl ether is added to the concentrated filtrate to remove insoluble matters and evaporated ether, thus the lipid is obtained.

It is dissolved in 1.5 fold of ethanol, pH of the lipid solution is adjusted with 50% KOH to above 10, saponified under nitrogen atmosphere, after its saponification is completed, filtered to separate the Kali salts of mixed fatty acids and unsaponified lipids. Its temperature is further decreased to 233°-243° K., to facilitate further the separation furtherly.

The saponified solution is acidified with 6N HCl or 50% $H_2SO_4$ to pH=3.0, extracted with ether, water layer is discarded, the ether layer of mixed fatty acids obtained is subjected to concentration to half of its original volume, stored in 253° K. refrigerator for 24 hr. filtered with filter paper at 273° K., the residue is further washed with ether, combined the filtrate, and washing solution concentrated to half volume and stored in 253° K. refrigerator for about 24 hours, filtered again. This operation can be repeated several times to separate and collect the solid saturated fatty acids and liquid unsaturated fatty acid. The components of solid fatty acid can be separated according their different freezing points.

EXAMPLE 15

Dry silica gel 85 parts and calcined gypsum 15 parts (premixed with CMC 0.5-100%, and starch 10-40%) are mixed thoroughly to form dry silica gel-calcined gypsum mixed powder. 3-4 parts water is added to the part of powder and triturated to form a paste, and coated onto a glass plate to form a thin layer, thickness of this layer may be 250 milli-micron (nm). The adsorbing capacity is about 10-15mg/cm². The coated glass plate is dried at ambient temperature, activated at temperature 353°-383° K. for 1 hour.

100% pure $AgNO_3$ is dissolved in small amount of water, to form a 10%-90% $AgNO_3$ solution. The plate with silica calcined gypsum thin layer are soaked into this solution for 30-120 sec, and dried in the dark. The saponified lipid solution (after acidified) is adsorbed on the plate. After adsorption, some non-polar solvents such as petroleum ether or hexane can be used as eluent to eluate the fatty acids, the eluate is treated with physiological salt solution to remove Ag ion, and subjected to separation to give various unsaturated fatty acids (with different ethylenic linkages). The saturated fatty acids may be collected from the eluate simultaneously.

As to the separation of various unsaturated fatty acids, various techniques can be applied such as adsorption, ultracentrifugation, ultrafiltration, freeze crystallization, chromatography, distillation, electrophoresis, ion-exchange, and the like. Other methods also can be used such as bromination-debromination, enveloped with urea, partitional solubilization, formation of $AgNO$ complex, and EDTA-NA composite method.

Some composite methods are illustrated in the following examples.

EXAMPLE 16

Mixed unsaturated fatty acids are dissolved in a suitable amount of methanol solution, urea is added in the proportion: unsaturated fatty acid: urea: methanol=1:3:7 (in weight), and stirred to dissolve urea, cooled under dry ice or liquid nitrogen and freeze crystallized according to the different freezing point of unsaturated fatty acids e.g. at 103°-273° K., filtered, the filtrate is dried over anhydrous $Na_2SO_3$, evaporating off methanol, various unsaturated acids can be separated.

EXAMPLE 17

The methyl ester of various unsaturated fatty acids are first prepared. 10 fold amount of 1 mol/L of alcoholic KOH is added to the methyl ester, heated to reflux under N at 313°-353° K. water bath for half an hour.

After hydrolysis is complete, it is concentrated at reduced pressure to remove a portion of $CH_3OH$, 3 fold amount of water is added to it, acidified with 4 mol./l HCl to pH 3.0, extracted with ethyl ether. The other layer is washed with water to pH 5-with ethyl ether. The ether layer is washed with water to pH 5-6, dried over only $Na_2SO_4$, and evaporated under $N_2$ and reduced pressure. After the ether is dried, the residue is subjected to freezed crystallization, to get various pure unsaturated fatty acids, kept under nitrogen, cold storage with protection of light.

As for liposoluble Vit A, D and E can be obtained from market, they also can be extracted from unsaponified lipid solution, but their cholesterol must be separated prior to extraction and the content must be determined before application.

In the preparation of CHML of this invention, the ultra-violet light and laser is used to convert the trace amount of cholesterol in the components into molecular lipid squalenes. The molecular lipid squalenes can't be conveniently obtained directly, but it can be as obtained by activation of cholesterol solution with uv light or laser, thus these kinds of molecular cholesterol lipid can be readily obtained with an economic procedure and cholesterol (with side effect to human body) can be converted into molecular lipid which is of benefit to the human body. That is the important and peculiar features in this invention, for example:

EXAMPLE 18

The double bond on α-site of cholesterol can be dehydrogenated by means of light energy, cholesterol can be converted into squalene. The synergistic effect of injury to cancer cell is enhanced about 50% by the CHML in this invention with application of these methods.

Chemical reaction is as follows:

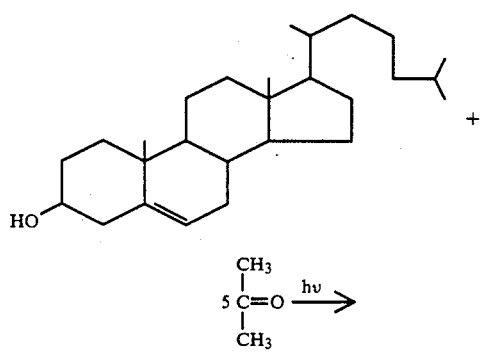

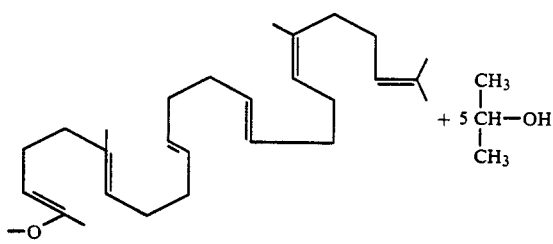

Cholesterol + acetone → squalenes + secondary alcohol Procedure. The unsaponified matters of animal oil and vegetable oil is extracted with acetone to get the cholesterol solution. To 100 ml of his solution (or other acetone solution of cholesterol) are irradiated with 30–100 w ultraviolet light lamp under atmospheric pressure directly, wave length of ultraviolet light = 2537 Å.

energy density = 20–100 mw.sec/cm$^2$, irradiated time = 50–10000 sec.

Temperature = 318°–348° K., pH of solution is 4–10, relative humidity = 55%. Evaporating off secondary alcohols after irradiation, the molecular lipid with squalene components is obtained.

Applying laser irradiation, the molecular lipid of this invention can be activated to get the optimum biological effect. For example, eicotrienenoic acid, eicotetraenoic acid and eicopentaenoic acid are activated with laser, they can be converted to prostaglandin, vit. A can be convert to retinal, α-tocopherol in vit. E can be converted to α-tocopherol, prostaglandin E can be converted to prostaglandin F. (This reaction can proceed in reverse direction under certain conditions).

The injury of human normal cell by molecular lipid is reduced as small as possible when laser irradiation, which is applied in this invention, and its bio-availability in human body is enhanced.

For example, docosahexenoic acid provides the anti-hypertension effect to human, but it can injure the endothelial cell of blood vessel, and the dissolution of cells may occur. In the preparations of this invention with the application of laser irradiation, the long chain unsaturated molecular lipid can be cyclized at α-site double bond in small portions, not only the requirement of human is attained, but the injury of normal cells can be reduced also. As the polyenic unsaturated fatty acid with 18°–30° C. carbon atom can be hydrogenated and cyclized at α-site double bond by means of laser irradiation.

The laser used in this invention is preferably a: ruby laser, Nd glass-laser transmitter Nd$^{+3}$ laser, YAG laser, He-Ne laser, CO$_2$, laser, Argon ion laser, Nitrogen molecular laser and Helium-cadmiun laser and the like.

The laser used in this invention is preferably a: ruby laser, Nd glass-laser transmitter Nd$^3$ laser, YAG laser, He—Ne laser, CO$_2$, laser, Argon ion laser, Nitrogen molecular laser and Helium-cadmiun laser and the like.

The application of laser irradiation may be performed along with animal microsome enzyme, prostaglandinase, Vit. C etc. for example.

EXAMPLE 19

The prostaglandin E is converted to prostaglandin F from prostaglandin E with laser irradiation in the presence of Vit. C., i.e. the keto form of prostaglandin is converted to enol form, the reaction scheme is as follows:

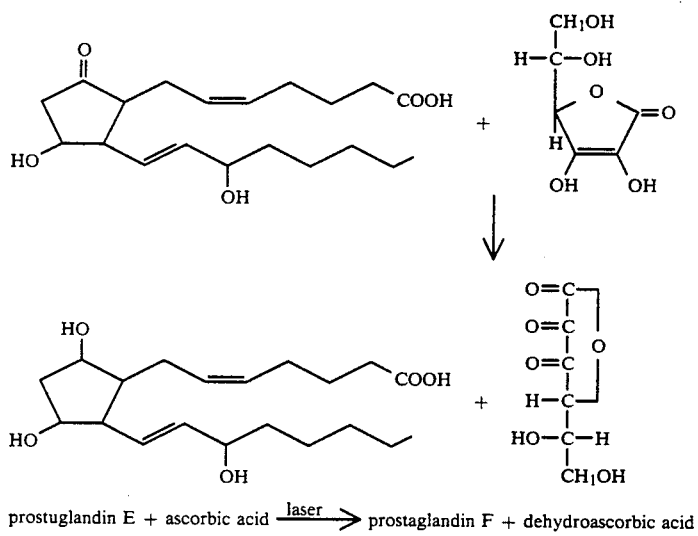

prostuglandin E + ascorbic acid —laser→ prostaglandin F + dehydroascorbic acid

Procedure: pure prostaglandin E (PGE) (taken from refrigerator) 1 g, is adjusted to pH = 8, standard Vit. C solution 0.05–15 g is added, stirred under N, and subjected to laser irradiation at 303°–311° K. The lasers used are He-N Laser, YAG Laser, or N molecular laser, wave lengths are 6328 Å, 10660 Å and 3371 Å respectively and their synthetic waves, power density 0.2–50 mw/cm$^2$ irradiation time of treatment = 10–180 min. As this reaction is ceased, the reaction mixture is subjected to centrifuge at 5000–100,000 rpm, supernatant is discarded, the residue is freeze crystallized to get activation and conversion contains precise molecular structure and excellent bio-effect.

EXAMPLE 20

The molecules of docosahexenoic acid (DHA) can be hydrogenated and cyclized by means of microsomelenzyme of sheep's seminal vesicle and Laser irradiation.

The reaction scheme is as follows:

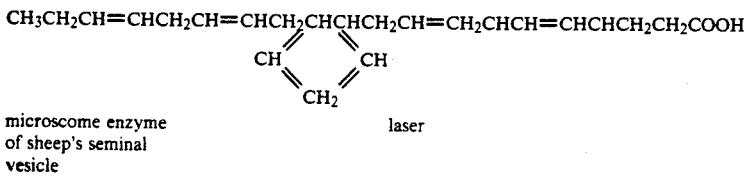

microscome enzyme of sheep's seminal vesicle ... laser

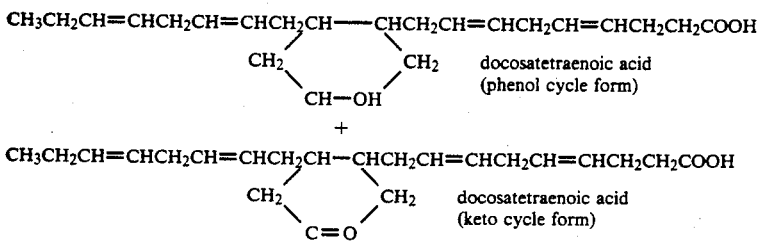

Procedure:
First step. Preparation of enzyme solution:

Sheep's seminal vesicle is taken from cold storage at 233°-253° K., its fat and connective tissues are removed, 1 l 0.154M of KCl solution is added per Kg. of seminal vesicle, crushed and homogenized to give a homogenized suspension, centrifuged at 600 rpm for 10 minutes the supernatant is discarded, further centrifuged at 10,000 rpm for 20-40 minutes, acidified with 2M citric acid to pH 46-5.6, centrifuged at 10,000 rpm, for 30-60 minutes, the supernatant is discarded.

The sediment is washed out with 100 ml 0.2M phosphate buffer (pH 8) EDTA-2Na solution is added to the mixture, 2M KOH is added drop wise to pH 7.5-8.2, cold storage in refrigerator, at 233°-243° K., that is the enzyme preparation.

Second step. the molecules are cyclized with hydrogenization:

Suitable amount of hydroquinone and glutathione are dissolved in a small amount of water and added into the 1 l enzyme preparation. 1-15 g Docosahexnoic acid (DHA) is added to the preparation of 1 kg sheep's seminal vesicle, under stirring and bubbling with oxygen. It is subject to laser irradiation with He Ne laser (wave length 6328 Å) power density: 0.1-50 mw/cm², depth of solution=0.63-6.22 mm.irradiation time: 5-60 min. temp. 310°-311° K. After the reaction is ceased, the heated mixture is cooled slowly, 2 mol.L hydrochloric acid is added along the wall of the apparatus to pH 4.0-4.2, centrifuged at 10,000 rpm for 30 min. To the sediment is added 3 fold amount of acetone, adjusted to pH 7 with aqueous ammonia, crushed and homogenized for 10-30 min. filtered under suction, press it to dry. This operation is repeated several times to get the filtrate. 2 mol/l. phosphate buffer is added to the filtrate to adjust pH to 8, the aqueous layer is defatted with petroleum ether, acidified with 2mol/lHCl to pH 3.0, extracted with $CHCl_3$ extracts are washed with water to remove the free acid, evaporating off $CHCl_3$, cyclic docasahexeenoic acid is produced, then subjected to chromatographic purification by means of $AgNO_3$-silica gel as adsorbent, ethyl acetate as developer, the eluent obtained is treated with physiological salt solution to remove Ag+, dried over anhydrous $Na_2SO_4$, filtered and the filtrate is concentrated under $N_2$ atmosphere and reduced pressure, ethyl acetate is removed, lyophilized to get pure cyclized docasahexenoic acid products.

The molecular lipids obtained as above are precisely analyzed with the technics of u.v. spectrometry, gas chromatography, mass spectrography, nuclear magnetic resonance, infrared spectrometry and laser spectrum analysis for determination of their molecular structure, and purity. Then various molecular lipids are purified by means of their fine filtering and recrystallization.

Finally, according to their necessities of various bio effect, they can be formulated into different preparations. The formulation included accurately weighed components of molecular lipid mixed with other molecular lipids, to which suitable amounts of additives as above are added, thoroughly mixed at 303°-353° K. for 10-30 times, decrease temp. to 288°-298° K., filtered through sinter glass filter. The filtrates can be directly used as the CHML of this invention. They have good quality and excellent effects.

CHML of this invention can be made in various preparations used for synergetic treatment or prophylaxis of cancer. CHML-V and Y are conventionally selected as medicament. They can be used as carrier of some antitumor drugs, such as 5-fluorouracil, Ping Yang Mycin in administration and exert the synergetic effect of "1st attack" and "2nd attack" to the cancer cells. Both CHML-C and CHML-H possess the effects of antivirus and anti hypertension respectively.

The medicated forms, starting materials, dosages of medicaments administration for and method of their preparations are illustrated in the following Examples.

EXAMPLE 21

1.2 g tetradecanoic acid, 11 g oleic acid and 0.06 g Vitamin A were mixed and heated to 333°-363° K. in a water bath, 28.32 ml water solution of 10% Mg (OH)$_2$ was slowly added dropwise under agitation for half an hour, 49.04 ml water and 0.2% (g/ml) active carbon were added and heated to 373 K, boiling for 30 minutes, filtered out active carbon, perfused and sealed into ampules under vacuum or nitrogen atmosphere.

EXAMPLE 22

3.2 g palmitic acid, 7.1 g palmitoleic acid, 8.5 g oleic acid and 0.04 g Vitamin D were mixed and heated to 333°-363° K. in a water bath. 26.8 ml water solution of 28.5% Ca(OH)$_2$ was slowly added dropwise under agitation for 45 minutes. 67.36 ml water and 0.2% active carbon were added and heated to 373.K, boiling for 30 minutes, filtered out active carbon, perfused and sealed into ampules under vacuum atmosphere.

EXAMPLE 23

0.7 g palmitic acid, 0.9 g stearic acid, 3 g palmitoleic acid, 6 g oleic acid, 3 g linoleic acid, 3 g linolenic acid, 2 g eicosenoic acid and 0.8 g Vitamin E were mixed and heated to 333°–363° K. in a water bath, 34.8 ml water solution of 10% KOH was slowly added dropwise under agitation for 30 minutes, 306 ml water and 0.1% active carbon were added and heated to 373.K, boiling for 30 minutes, filtered out active carbon, perfused and sealed into ampules under vacuum atmosphere.

EXAMPLE 24

3.2 g tetradecanoic acid, 3.4 g stearic acid, 2.8 g palmitoleic acid, 4 g oleic acid, 2.8 g linoleic acid, 2 g linolenic acid, 0.4 g eicosatetraenoic acid, 0.1 g Vitamin A and 0.1 g Vitamin D were mixed and heated to 333°–363° K. in a water bath, 35 ml water solution of 50% Zn $SO_4$ was slowly added dropwise under agitation for 45 minutes, 360 ml water and 0.2% active carbon were added and heated to 373 K, boiling for 30 minutes, filtered out active carbon, perfused and sealed into ampules under vacuum atmosphere.

EXAMPLE 25

0.6 g palmitic acid, 0.8 stearic acid, 4.7 g oleic acid, 5 g linoleic acid, 2.7 g linolenic acid, 0.2 g eicosadienoic, 0.5 g eicosatetraenoic acid, 0.3 g eicosenoic acid, and 0.14 g Vitamin E (Vitamin E had been hydrolyzed by steapsin) were mixed and heated to 303°–363° K. in water bath. 18 ml water solution of 25% HClO was slowly added dropwise under agitation for 45 minutes, 600 ml water was added, adjusted pH to 6.5 by HCl. 0.1% active carbon was added and the mixture was heated to 343°–363° K., maintained for 30 minutes, filtered out active carbon, perfused and sealed into ampules under vacuum atmosphere.

EXAMPLE 26

1.2 g palmitic acid, 1.2 g stearic acid, 3.6 g palmitoleic acid, 7.5 g oleic acid, 2 g linoleic acid, 1 g eicosatetraenoic acid, 1.1 g docosahexenoic acid, 0.25 g Vitamin E and 0.05 g Vitamin A (Vitamin E and Vitamin A had been hydrolyzed by steapsin) were mixed and heated to 393°–463° K. in a water bath, 32 ml water solution of 10% HF was slowly added dropwise under agitation under the pressure of 15 kg/cm² for 60–90 minutes, 330 ml water including 40 g perfluoro-butyltetrahydrofuran (FC-80), 14 g polyfluoronaphthalene (FDC) and trifluorotripropyl amine (FTpA) were mixed and maintained at 373°–463° K. for 3 hours, 0.2% active carbon was added and maintained at 373° K. for 30 minutes, filtered out active carbon, perfusd and sealed into ampules under vacuum atmosphere.

EXAMPLE 27

1 g tetradecanoic acid, 1.5 g palmitic acid, 1.5 g stearic acid, 2.5 g palmitoleic acid, 7.5 g oleic acid, 2.5 g linoleic acid, 1.5 g linolenic acid, 0.1 g eicosatetraenoic acid, 0.3 g docosahexenoic acid, 0.02 g prostaglandin, 0.6 g Vitamin E, 2.5 g ethanol, 0.16 g sulfuric acid and 440 ml water were mixed and heated to 413°–433° K. at a pressure of 5–10 kg/cm² for 4 hours under agitation, 0.5% active carbon was added at 373° K. and maintained for 45 minutes, filtered out active carbon, perfused and sealed into ampule under vacuum atmosphere.

EXAMPLE 28

0.2 tetradecanoic acid, 1.2 g palmitic acid, 0.7 g stearic acid, 0.7 g eicosanoic acid, 4 g palmitoleic acid, 6 g oleic acid, 4 g linoleic acid, 1 g linolenic acid, 0.1 g eicosatrienoic acid, 0.1 g eicosenoic acid, 0.1 g eicosadienoic acid, 0.1 g docosatetraenoic acid, 0.05 g docosahexenic acid, 0.05 g tetracosenoic acid, 0.2 g Vitamin E and 24 g arginine were mixed while blowing nitrogen gas. The mixture was heated to 343.K in a water bath. 0.02 g sulfuric acid and 0.14 g CH₃ONa were added slowly. The mixture was heated to 413°–453° K. and maintained for 30–60 minutes at a pressure of 5–15 kg/cm₂ under agitation. The temperature was decreased to 333° K. and maintained at this temperature for 3 hours. 0.1% active carbon was added and the mixture was kept for 30 minutes, filtered out active carbon, perfused and sealed into ampules under vacuum and nitrogen atmosphere.

EXAMPLE 29

0.1 g dodecane acid, 0.1 g tetradecanoic acid, 0.2 g palmitic acid, 0.2 g eicosanoic acid, 1 g palmitoleic acid, 5.6 g oleic acid, 3 g linolenic acid, 3 g linolenic acid, 1 g eicosatetraenoic acid, 1 g docosahexanoic acid, 0.5 g tetracosandienoic acid, 0.5 g tetracosantetraenoic acid, 0.07 g squalenes (see example 18 for the process for preparing squalenes), 0.2 Vitamin A, 7.4 guanine or 7.7 g 6-mercaptopurine and 0.98 g CH₃ONa were mixed and heated at 393°–453° K., 0.117 g sulfuric acid was added slowly under agitation at a pressure of 5–25 kg/cm² for 3–6 hours, thereafter the temperature was decreased to 343° K., 0.2% active carbon was added and maintained for 30 minutes, filtered out active carbon, perfused and sealed into ampules under vacuum atmosphere.

EXAMPLE 30

0.07 g squalene, 0.15 g τ-linolenic acid, 0.25 g linolenic acid, 2 g oleic acid, 0.7 g stearic acid, 0.75 palmitic acid, 1 g docosahexenoic acid (see Example 20 for the process for preparing), 0.5 g docosenoic acid, 0.15 g docosadienoic acid, 0.2 g docosatrienoic acid, 0.7 g docosatetranoic acid, 0.5 g docosapentanoic acid, 1 g palmitoleic acid, 0.4 g eicosatetraenoic acid, 0.9 g eicosapentaenoic acid, 0.3 g eicosatrienoic acid, 0.4 g tetracosenoic acid, 0.4 g Vitamin E, 0.01 g Vitamin A and 0.02 Vitamin D, 4.08 g uracil, 0.07 g sulfuric acid and 0.064 g CH₃ONa were mixed and heated to 393°–458° K. under agitation at a pressure of 5–25 kg for 3–6 hours. The temperature was decreased to 343° K., 0.2% active carbon was added for 30 minutes, filtered out active carbon, perfusd and sealed into ampules under vacuum atmosphere.

EXAMPLE 31

Tablet: It can be used mainly in treatment and prophylaxis of the pathologic change to cancer at earlier stages such as carcinoma of stomach, colon and rectal cancer, etc.

| Materials | Amount used per 160 tablets |
|---|---|
| CHML | 50 ml. |
| dextrin | 17.8 g |
| sugar powder | 10.2 g |

| Materials | Amount used per 160 tablets |
|---|---|
| talc powder | 1.5 g |
| magnesium stearate | 1.0 g |
| antitumor drugs | suitable amount is necessary |

Method of preparation: CHML is concentrated to 20-40% level, to which the anti-tumor pharmaceutical, sugar powder, and starch are added and ground together to form a paste, it is further mixed with other components, sieved to pass 160 mesh. and pressed into tablets.

EXAMPLE 32

Microcapsules: It is adapted for the synergetic treatment to the various systemic cancer and for prophylaxis of cancer is earlier stage, CHML-Y and CHML-V are preferred.

As for adapted to antivirus and anti-hypertension, CHML-C and CHML H are preferred. The dry small size microcapsules are soaked in the 10% CHML solution, after CHML is absorbed into it, and dried in a drying box, CHML-microcapsule preparation is obtained, ready for use.

EXAMPLE 33

Eye Drops

It may be adapted for synergetic treatment and prophylaxis of the eye disease infected with virus and precancerous stage cancer and carcinoma in eyes.

| Material | Amount |
|---|---|
| Formula 1 | |
| CHML | 50 mg |
| anhy. Na$_2$HPO$_4$ | suitable amount |
| anhy. NaH$_2$PO$_4$ | suitable amount |
| moroxydine hydrochloride (ABOB) | 4 g |
| distilled water | added to 100 ml |
| Formula 2 | |
| CHML-Y | 100 mg |
| Boric acid | suitable amount |
| Borax | suitable amount |
| antitumor drugs | as necessary |
| distilled water | added to 100 ml |

CHML and phosphate are mixed and warmed in small amount of distilled water, borax, boric acid, moroxydine hydrochloride or antitumor pharmaceutical are added and mixed with suitable amount of distilled water to the predetermined volume, perfused separately into dried, sterilized dropping bottles for eye drops.

EXAMPLE 34

Injection: the injection is adapted to synergetic treatment and prophylaxis of various benign tumor, malignant tumors (or carcinomas) and the precancerous stage. it is administered in local injection, i.v. injection and intravenous drop in the form of CHML preparations. They may contain or not contain anti tumor pharmaceutical, determined by the clinical physician.

Preparations for local injection, can be injected into the zone of pathologic change directly.

| Materials | Amount |
|---|---|
| CHML-Y | 10 g |
| ethanol (95%) | 2 ml. |
| antitumor drugs | suitable amount as necessary |
| distilled water | added to 100 ml. |

CHML is mixed thoroughly with distilled water and ethanol, then perfused and sealed in ampoules (1 ml or 2 ml). Specification: Each ampoule is perfused with 1 ml CHML preparation or 2 ml CHML preparation, sterilized by live steam at 373° K., ready for use.

The injection for i.v. and intravenous drip: The injection for i.v. is characterized in the synergetic therapy of strongly pathogenic change and systemic transference of cancer, e.g. according to the suggestion of the results of examination of freezes pathological section during the operation, it be suited the exigent treatment. The intravenous drip may be applied to the treatment and prophylaxis of leukemia. The content of CHML can be 5%, 10%, 15% and 20% respectively, material and dosage are same as above this example. When it is used in i.v. injection, 1 ml. of CHML preparation is diluted with 20 ml physiological salt solution as for intravenous injection, 1-2 ml of fresh CHML injection is diluted with 5% glucose containing physiological salt solution for intravenous drip.

EXAMPLE 35

Aurinasal Drops

It is applied to synergetic therapy and prophylaxis for the precancerous stage and cancer in nasal cavity and ears, especially for treatment of nasopharyngeal carcinoma

| Materials | Amount |
|---|---|
| CHML-Y | 250 mg |
| peppermint crystal | 1 g |
| ping yang mycin | suitable amount as necessary |
| liquid paraffin | added to 100 ml. |

CHML, suitable amount of Ping Yang mycin, peppermint crystals are put together in a mortar, liquid paraffin is added, ground and mixed thoroughly, liquid paraffin is further added to the required volume, ready for use.

EXAMPLE 36

Aerosol

It is applied to synergetic therapy and prophylaxis for lung cancer, is applied to synergetic therapy and prophylaxis for bronchial cancer and esophageal cancer.

| Materials | amount used for 20 bottles of aerosols |
|---|---|
| CHML-Y | 60 ml. |
| lemon essence | 1 ml. |
| 7% ethanol | 56 ml. |
| saccharin sodium salt | 4 g |
| 5-fluorouracil (5-Fu) | suitable amount as necessary |
| dichloro diflouro ethane | 160 ml. |

CHML and 7% ethanol are warmed together to 313°-333° K., cooled to 283° K. subsequently, lemon essence and 5 Fu are added, thoroughly mixed and perfused into aerosol bottle separately. Dichlordifluroethane is pressed with it, sealed, ready for use.

When CHML in this invention are used as carriers with carrying a small amount, or even very small amounts of drugs, it can exert the strong synergistic effect. It is so called "Bio-molecular missile". It has been confirmed by a lot of pharmacologic research that it works. For example, inhibition to S-180 Sarcoma cells in vivo, effects on B-cell, preclinical pharmacologic research work, Ames test, determination of conventional dosage and limitary dosage, etc., have been examined. Results are as follows:

I. The Experiment of Inhibitory Effects of CHML-Y on S-180 Sarcoma Cells

CHML-Y may obliterate whole S-180 sarcoma cells in vitro.

This may show strong Bio-effect of CHML.

Materials:

CHML-Y provided by inventor, 0.5% content
Incubating liquid RPM1-1640 (liq.) S-180 Sarcoma cell provided by Shanghai Cancer Institute.

Method

The mice were inoculated with S-180 cells and raised for 7 days. They were killed by drawing their necks. S-180 cells containing ascite were drawn out, a small amount of RPMI-1640 was added, the numbers of S-180 cells in ascitie are counted. RPMI-1640 was further added to adjust the cell content in $5 \times 10^6$/ml. 1.5 ml. of above incubating liquid was transferred to each test tubes (Total = 10 tubes).

5 tubes served as control and 5 tubes for examination of experiment. RPMI-1640 incubating liquid was dropped in 0.2 ml/tube for control and 1 mg of CHML-Y was dropped into each tube containing the incubating fluids covered, reposited in 37° C. thermostatic water bath, centrifugalized over every 10 min. interval, the sediment was taken and examined smears with Wright's staining method. This experiment was performed in triplicate. The results were shown in table 2.

TABLE 2

| groups | dosage (CHML-Y) | cell counting/ml | mortality of S-180 cell (%) | | | | |
|---|---|---|---|---|---|---|---|
| | | | 10 min. | 20 min. | 30 min. | 40 min. | 50 min. |
| control | — | $5 \times 10^6$ | — | — | — | — | — |
| experiment | 1 mg/ml | $5 \times 10^6$ | 50 | 60 | 70 | 85 | 100 |

The morphological change of S-180 cells treated by CHML-Y is shown in FIG. 3(a) to FIG. 3(d).

The dosage of appropriate components or concentrations of CHML-Y can be selected for killing the cancer cell within 2-3 seconds, but it also exhibits the injury of human healthy cell, to a certain extent. It is preferable to control the components and concentration of CHML-Y to a certain level to cause injury to cancer cells and maximally decrease the effect of injury to normal human cells.

II. The Experiment of Effect of CHML-A on B Cell With CHML-A

This experiment can be confirmed that CHML-A is a of molecular bio-immunological enhancer, especially for the immunofunctions of B cell.

Materials

CHML-A provided by the inventor, concentration—10%,
Incubating medium: RPMI-1640 powder form, diluting according to standard method, pH 6.8, containing penicillin 100 µg/ml, streptomycin 100 µg/ml.
Animals: JCR mice provided by Shanghai second medical University, animal house.

Methods

1. Hemolytic Plaque Forming Cell on Spleen (PFC/Spleen)

32 JCR mice, (their average body weight is about 20 g.) are optionally divided into 3 groups, first group is used for control, injected in caudal vein intravenously with physiological saline 0.2 ml/each mouse, second and third groups are injected into the caudal vein (intravenously) with CHML-A preparations, dosage: 25 mg/kg & 50 mg/kg respectively. After the drug administered for 10 min., injected with sheep erythrocyte, (SRBC) suspension 25%. The mice are raised for 4 days. They are killed by exsanguination, their spleens are taken out, homogenized in a glass bead homogenizer to get the cell suspension. RPMI-I640 incubating medium is added into it, centrifuged, and washed. The suspension is adjusted to a concentration of $2 \times 10^6$/ml of cells, SRBC 25% 0.1 ml is added to 0.5 ml suspension, 0.1 ml of sample diluted to (1:2) with lyophilized serum of Guinea pigs and 0.15 ml of incubating liquid. Coated on the glass slide to establish nonlayer cell suspension, incubating 37 C for 60 mins.

The number of plaque forming cells counted under stereoscopic microscope, the results are shown in Table 3.

TABLE 3

| groups | CHML-A dosage mg/kg. | number of mice initial | number of mice final | sex | PFC/spleen | P* |
|---|---|---|---|---|---|---|
| control | N.S.iv. | 16 | 16 | female | $5.98 \times 10$ $\pm 0.61 \times 10$ | — |
| therapeutic (1) | 25iV. | 8 | 8 | female | $8.29 \times 10$ $\pm 1.41 \times 10$ | <0.01 |
| therapeutic (2) | 50iV. | 8 | 8 | female | $9.57 \times 10$ | <0.01 |

2 Determination of Spleen Index in Mice.

24 mice JCR, average body weighed 20 g, are divided into 3 groups optionally, 8 mice per group, one group is the control group, every mouse is treated (i.v.) with physiological saline 0.4 ml/day. Another two groups are therapeutic groups, every group is administered (I.V.) with CHML-A preparations 25 mg/kg & 50 mg/kg respectively per day. The administration is continued for four days. The mice are dissected, take out the spleen, weighed, spleen index is calculated according the following formula:

$$\text{spleen index} = \frac{\text{wt. of spleen}}{10 \text{ g. of body weight}} \times 100\%$$

The results are shown in table 4 below.

TABLE 4

| groups | CHML-A dosage (×days) mg/kg | Numbers of mice initial | Numbers of mice final | Spleen index | P* |
|---|---|---|---|---|---|
| control | N.S. (×4)iV. | 8 | 8 | 61.05 ± 4.45 | — |
| therapeutic (1) | 25(×4) iV. | 8 | 8 | 79.02 ± 8.78 | <0.01 |
| therapeutic (2) | 50(×4) | 8 | 8 | 98.90 ± 17.28 | <0.01 |

Note *test of significance

The results of 2 experiments as above show that CHML-A preparation provides the promotive effect of B-cell function. This is the basis for transmission to clinical trial.

III. Preclinical Pharmacological Experiments of CHML on Animals

The sources of CHML of this invention are derived from the cells of normal plants and animals, their components are liquids acceptable by human body. According to the literature cited, their toxicities are very low under suitable amounts administered. The results obtained from toxicity test in animals are shown below.

Acute toxicity test (examination period is two weeks after injection)

30 mice, average body weight is about 15 g. 2 months old mice are divided into 3 groups optionally, 10 mice for each. The control group are subcutaneously injected into the caudal vein of the mice with 5% glucose saline 1.5 ml. Whereas 2 experimental groups are injected into the caudal vein of mice with 25 mg/kg and 50 mg/kg CHML plug 5% glucose saline 1 ml respectively. Their mobility are examined. It is examined whether mice closure of hairs, refusal of food, marasmus gradually to death will appear or not, whether side effect of cardiovascular, respiratory tract, digestive tract will appear or not. The results of higher dosage group (experimental) suggested that 20 min to 48 hrs. after treatment, only a slight effect has been observed in cardiovascular, respiratory tract, digestive tract in some mice, but mobility are kept in normal state, no relaxations or deluster of hairs observed after 48 hrs, eat violently after 72 hours, no marasmus and death occurred. The side effect of lower dosage group are more slight, $LD_{50} = 4836 + 196.4$ mg/kg.

24 Rabbits (average body weight 2.3 kg) are divided into 3 groups, 8 rabbits for each group. In the experimental group, 10-30 ml of 1% CHML and 5% glucose saline 2 ml are injected (i.v.) into the subcutaneous vein (at the back of the ears) respectively and examined the basal body temperation and local and systemic side effects. The basal body temperature is detected by a portal thermometer, average body temperature is 38.2°±0.2° C. before injections and 38.2°±0.4° C. in 48 hr after injection. In the higher dosage group, a slight local blood clot is formed in the vein of 8 rabbits and slight tubefaction in the local site and local temperature is raised, when subjected to 24-72 hrs. tumefaction is disappeared, body temperature is normal, no infections in tissue, no necrosis is observed. Systems examinations: respiration and heart rate is increased during injections for 30 minutes, slight decreased appetite is observed as the side effect of digestive tract, but appetite is enhanced after 72 hours, no abnormalities are observed at nerve system, the lustrousness of hairs are in normal. No marasmus and death are observed.

2. Subacute Toxicity Test (examinmatorial period 2 weeks to 6 months after injection); 30 rabbits, average body weight about 2 Kg, female:male—15:15, are divided optionally into 3 groups, the one is for control and another 2 groups as experimental, 10% glucose solution 3 ml are injected (i.v.) into the subcutaneous vein (at the back of ears) as control. 25 mg/kg and 50 mg/kg CHML plus 10% glucose solution 4 ml are injected (i.v.) into the subcutaneous vein (at the back of the ears) as experimental respectively, their blood pressure, heart rate, side effect in the nerve system and digestive systems are examined. Their body weight, hemoprotein content, erythrocyte counting, leukocyte counting, conventional analysis of urine, functions of liver and kidney and other organ are also examined by pathological methods and by naked eyes.

Results of experimental group. The body weight and leukocyte counting are increased slightly except the blood pressure tends to decrease. Heart rate increased after 48 hrs. no abnormalities are observed in the nerve system, slight anorexia is observed at the effect of digestive tract but appetite is enhanced after 72 hours, no death is occurred.

The results of hemoprotein content, erythrocyte counting, leukocyte counting, conventional urine analysis, functions of kidney, liver and other organs are normal by examination of pathological slides and by eye inspections.

Special toxicity test (period for inspections 1 month to 6 months) 18 female mice (about 2 weeks prior to pregnancy) average body weight about 18 g, are optionally divided into 3 groups, 6 mice per group, one group serves as control injected (i.p.) with 5% glucose saline 2 ml/mouse, another two groups serves as experimental are injected (i.p.) with 50 mg/kg and 100 mg/kg CHML+5% glucose saline 1 ml respectively. Examination: The newborn mice are examinated.

The results show no abnormality is observed in newborn mice, the digestive tract and nerve system are normal, their developments are same as control group.

6 female dogs, average body weight 18.5 kg (about 2 months postpregnancy) are divided into 3 groups optionally, one group serves as control, injected (i.p.) with 5% glucose saline 8 ml/day. Another 2 groups serves as experimental, injected with 100 mg/kg and 200 mg/kg of CHML and 5% glucose saline 4 ml respectively.

Examinations: The newborn dogs are examined

The results shown no abnormality is observed in newborn, dogs, in the experimental group, their digestive tract and nerve system are in normal, developments are same as control group.

4. Test For Side Effect of Local Site in Animals (1) Test on Skin

The results of the test for cutaneous side effect on mice (Kunming species) and rabbits show no side effect under the dosage of CHML 5% 20 ul/mm².

(2) Test on Nose-Drops

No side effect is appeared in the naso-mucosa of the mice under the dosage 2.5% CHML 2 ml per mouse every time.

(3) Test of Eye-Drops

No side effect is appeared in the eyelid conjunctiva and eyeballs of rabbits, under the dosage 0.5% CHML 0.1 ml/eye every time.

Ames Test for CHML

Identification of Strains

Histidine deficient mutant strain of Salmonella typhimurium: TA98 and TA100 with R-factors (separately) are used as test strains, the strain is examined for the requirement of histidine for growth spontaneous reversion test, test for deletion of repairing system ($UV_rB$), test for deletion of barrier of lipopolysaccharide (rfa) and the test for the resistance to ampicillin be used as standard test to examine proof strains.

The strains are inoculated in the broth culture at 37° C. for 16 hrs. prior test. The viable count of the cell suspension must be maintained at $10^8$–$10^9$, it can be used for determination of mutagenesis.

Preparation of S-9 Mixture

Male rats (average body about 150 g) are administered with polychlorobiphenyl (Aroclor 1254) which is diluted with corn oil, dosage 500 mg/kg for 5 days. The rats are dissected and the livers are taken out and homogenized to get 9000 g homogenized suspension. It is then subjected to centrifugalization, the supernatant is brought to process to S9. It is freeze-stored in liquid N.

During utilization, S-9 mixture is made by addition of S-9 0.3 ml. $MgCl_2$ 8 μmol. KCl 33 μmol. G-6-P: 5 μmol NADP 4 μmol and pH=7.4 phosphate buffer solution 100 μmol per 1 ml of S-9 mixture. The amount of S-9 mixture used for examination is 0.2 ml/dish, (about S-9 40 μmol). These operations must be carried out under aseptic condition and the microsome activated systems of rat's liver must be added during examination.

Control of Mutagenesis

The CHML sample is diluted to a series of concentrations (5 μg –500 μg/me) with dimethyl sulfoxide (DMSO), 3 Petri dishes are taken for each concentration for test. The basic incubating medium (U-B low concentration liquid) 15 ml are added to each dish. After coagulation, (2 ml of upper layer incubating medium), 0.1 ml of bacterial suspension, sample of each concentration to be examined 0.1 ml (the concentrations of the sample per dish are 0.5, 5, 50, 500 & 5000 μg respectively) and S-9 mixture 0.2 ml are also added together into the upper layer of incubating medium 2 ml. After coagulation, they are incubated at 37° C. for 48 hrs. The reversed mutant colonies are counted.

Besides the spontaneous reversion the bacterial suspension added with S-9 only are served as negative control, the cyclophosphamide and diacetylamino fluorene are used as negative control also.

TABLE 5-a

| Test sample | test dosage μg/dish | mutagenesis TA98 | TA100 |
|---|---|---|---|
| CHML | 0.5–5,000 | − | + |
| Cyclophosphamide (CTX) | 1,500 | | + |
| diacetylamio fluorene (2AF) | 200 | + | + |

TABLE 5-a-continued

| Test sample | test dosage μg/dish | mutagenesis TA98 | TA100 |
|---|---|---|---|
| Spontaneous reversion | | − | − |

TABLE 5-b

| Test sample | test dosage μg/dish | Numbers of reversion colonies (average) TA98 | TA100 |
|---|---|---|---|
| CHML | 0.5 | 26 | 203 |
| | 5.0 | 13 | 233 |
| | 50.0 | 18 | 146 |
| | 500.0 | 24 | 125 |
| | 5000.0 | 17 | 137 |
| Cyclophosphamide (CTX) | 1500 | | 519 |
| diacetylamino fluorene (2-AF) | 250.0 | 254 | |
| numbers of spontaneous reversion | | 28 | 155 |

Discussion

These experiments as above have confirmed that no reverse mutation occurred against test organisms by various components of CHML preparations in this invention, and further evidenced that the mutation of codons and the mutation of base pair replacement can't be induced also.

V. Conventional Dosage and Limiting Dosage of CHML-Y

The results shown as follows:

| Mouse (Kunming sp.) | | |
|---|---|---|
| i.v. administration | conventional dosage | 25 mg/kg |
| i.p. administration | limiting dosage | 150 mg/kg |
| Rabbits | | |
| i.v. administration | conventional dosage | 50 mg/kg |
| i.p. administration | limiting dosage | 400 mg/kg |

Monitoring the Membrane Molecular Structure of the Leukocyte Leukemia Patients By CHML-M About 20 years ago, it has been proved that the flowability of leukocyte membrane of leukemia patients are higher than that of normal. This is mainly due to the unsaturated molecular lipid content in the leukocyte membrane of leukemia patient are increased, while the saturated molecular lipid contents in the leukocyte membrane of leukemia patient are decreased. Thus the viscosity of the membrane is increased. According to the fact that the flowability of leukocyte membrane of leukemia patient is increased and the ability of adsorption and absorption of CHML-M is decreased, a novel reagent and method for the monitoring of molecular structure of cell membrane by CHML-M are designed. This method is simple, rapid, and correct.

Materials

CHML-M standard reagent is provided by inventor, concentration: 3 mg/ml.

Incubating medium: RPMI-1640 incubating liquid.

Blood specimen (normal) taken from healthy volunteers, blood specimen of leukemia patients are taken from leukemia patients by diagnosis in hospital.

Apparatus—Ultra violet spectrometer with scanning (philips PU8800, and 753 made in China)

Procedure

1. Collecting of blood: Fresh normal blood 2ml is placed in a test tube containing 40 heparin, shaked and mixed gently.
2. Sediment of leukocyte: sedimentation of leukocyte in said 2 ml fresh normal blood is carried out by natural sedimentation. The test tubes are stayed uprightly at 37° C. thermostat for 30–60 min.
3. Washing of cells. The leukocytes are settled at the upper layer, while the erythrocyte are in the under layer, take out the upper layer of leukocytes, then leukocytes are transferred into RPMI-1640 incubating liquid, centrifuged in 1000 rpm. washed 3 times.
4. Leukocyte counting: The supernatant is discarded, leukocytes are taken out carefully by means of a capillary, according to leukocyte counting counted and regulated to the concentration of leukocytes to $1 \times 10^6$/ml.
5. Separating into test tubes: the suspension is mixed gently and divided into 2 test tubes i.e. one tube for control and other for experimental examination, these is leukocyte suspension 0.9 ml in each test tube.
6. 0.1 ml of physiological salt solution is added into the test tube for control, and 0.3 mg of CHML-M preparation is added into the tube for examination.
7. Incubation and evaluation: the mixture in the test tube is incubated at 37° C. thermostat for 120 min. centrifuged under 1000 RPM for 10 min. 0.5 ml aliquot of supernatant is taken, and 4.5 ml of distilled water (by triple distillation) is added. The solution is subjected to UV spectrometer for the determining the CHML-M.

Results: The results of scanning of CHML-M absorption curve in different U.V. wave length are shown in Table 6.

TABLE 6

| System No. | Wave length | O.D. | Ratio of Diffusion |
|---|---|---|---|
| 001 | 257.2 | 1.221 | 1:50 |
|  | 254.6 | 1.152 | " |
|  | 236.1 | 1.607 | " |
|  | 228.0 | 1.552 | " |
| 009 | 236.0 | 0.188 | " |
| " |  | 1.604 | " |
| 009 | " | 1.602 | " |
|  | " | 0.944 | 1:100 |
|  | " | 0.459 | 1:200 |

The standard curves of CHML-M standard reagent designed by this invention are shown in FIG. 4.

The results for monitoring the membrane structure of leukocyte by CHML-M with UV spectrometer are shown as Table 7.

TABLE 7

| Group | Numbers of Cases | Sex | Years Old | Cell Count | CHML-M X + SD (μg/ml) |
|---|---|---|---|---|---|
| normal | 63 | male | 20–40 | $1 \times 10^6$ | 7.819 ± 2.119 |
| normal | 65 | female | 20–40 | $1 \times 10^6$ | 7.384 ± 2.394 |
| AGL | 16 | male:female 6:10 | 20–40 | $1 \times 10^6$ | 31.01 ± 4.146 |
| CGL | 7 | male:female 3:4 | 20–40 | $1 \times 10^6$ | 21.11 ± 2.714 |

Notes:
AGL: acute granulocytic leukemia
CGL chronic granulocytic leukemia

The monitoring of molecular structures of membrane of leukocyte for leukemia by means of the CHML-M designed in this invention gives accurate results, the preliminary experimental results suggest the method in this invention is valuable in practice for development.

XII. The Phagocytosis Test of Alveolar Macrophages in Rabbits

1. Extraction of Alveolar Macrophage 6 healthy rabbits (female:male=3:3) are chosen.

Their average body weight is 3 kg. Their lungs along with distal trachea are extracted under anesthesia, suspended the lungs in a glass disc containing 0.01M PBS (phosphate buffer solution pH 7.4, 30 ml washing solution (pH 7.4 0.01M PBS) is perfused into trachea by means of 50 ml syringe and drawn out again. This operation is performed 3 times. The amount of the drawn off liquids are recorded. Each liquid is combined, then perfused into a bottle, cold storage, ready for use.

Cell counting, above washing solution 0.5 μl is placed on a glass slide, mixed well with equal amount of trypan blue added and dropped into a cytometer, the total number of alveolar macrophage is counted, according to the method of counting for the leukocyte.

The 1st recovery of washing solution is attained to 84.6% 2nd at 96.6% and 3rd of 98.3%. The total count of the rabbit's alveolar macrophages (6 rabbits) are $2.5 \times 10^5$/ml, living cells=93.5%.

There are alveolar, macrophage (average) 92.4%, cosinocyte 65%, lymphocyte 0.9%, neutrophil leukocyte 0.4% in the washing solution.

2 Bacterial Phagocytosis Test

Control group: 8 ml of washing solution are mixed with 4 ml.

B. Candida Albicans suspension (30,000,000 bac/ml), incubated at 37 for 30 min. centrifugalized 10 min at 1000 rpm, the sediment is spread onto a glass slide to form smears, stained with Wright's staining method staining and HE staining, examined under microscope.

Experimental Group 8 ml of washing solution are mixed with 4 ml candida albicans suspension ($3 \times 10^7$ bac/ml) for 10 minutes, 5% CHML 10 1, 10% CHML 10 1 are added separately incubated at 37° C. for 20 minutes, centrifugalized at 1000 rpm for 10 min. The sediment is spread onto a glass slide to form smears, stained with Wright's staining method and HE staining, examined under microscope, to calculate and record the percentage of phagocytosis and phagocytic index as follows.

$$\text{percentage of phagocytosis} = \frac{\text{number of alveolar macrophage for phagocytosis of bacteria}}{200 \text{ alveolar macrophage}} \times 100\%$$

$$\text{phagocytic index} = \frac{\text{number of bacteria phagocytosized by 200 alveolar macrophages}}{200 \text{ alveolar macrophages}}$$

These results are shown in Table 8.

TABLE 8

| Groups | percentage of phagocytosis | Phagocytic Index |
|---|---|---|
| control | 6.3 ± 4 | 0.09 ± 0.07 |
| experimental | 10.0 ± 6 | 0.14 ± 0.08 |

XIII. The Effect of CHML-Y on Squamous Carcinoma of Human Esophagus In Vitro

Materials and Methods

Same as the experiment for killing of S-180 sarcoma cells with CHML-Y preparations. The experiment are carried out in triplicates. The results are shown in Table 9.

TABLE 9

| Groups | Dosage | Numbers of Cancer Cells | Mortality of Cancer Cells (%) 10 min. | 20 min. | 30 min. | 40 min. |
|---|---|---|---|---|---|---|
| control | — | $5 \times 10^5$ | — | — | — | — |
| experimental | 1 mg/ml | $5 \times 10^5$ | 60 | 80 | 95 | 100 |

It is evident that CHML of this invention is a series of "bimolecular missile". The results of the inhibition test of human cancer cells with CHML (in vitro) and a series of experiments provide a valid basis for the feasibility studies on the clinical trials.

According the studies on mechanism; the degree of oxygen dissociation in tissue cells are decreased while the content of CHML is attained to 0.1 mole/g, but the ability of carrying oxygen by CHML is increased. When the CHML content is attained to 19 mole/g, the degree of oxygen dissociation in tissue cells is increased, the abilities of CHML for oxygen carrying is decreased significantly. During the mutations of tissue cells, suitable concentration of CHML entered into mutant cell, large amount of oxygen is absorbed by CHML. The oxygen deficiency within the mutant cell is made apparent, the oxidative phosphorylation of mitochondrion is blocked, ATP decreased, and the synthesis of protein nucleic acid is blocked, the binding of cancer to CHML is increased. The function of endoplasmic recticulum is blocked. Thus the mutation of cells can be inhibited.

IX. Experiment of the Inhibitory Effect of CHML-C on Virus

The virus developed on the tomatoes are tomato mosaic tobamo-virus (TMV.), cucumo virus (CMV) and patato virus X. The morbility caused by these virus approximately 95:23:2.

CHML-C functions as antiviral agent and as carrier to carry the antivirus drugs into the plant cells also at the same time, CHML-C provides the enhancement of resistance of plants.

The CHML-C of this invention is applied to the infection zone by virus in tomato. The aim of this experiment is to examine the effect for inhibition and prophylaxis of virus infection in tomatoes to protect from virus infection and degeneracy of tomatoes.

Material and Methods

CHML-C is provided by inventor.

In the open-air field, where the tomatoes bearing with inlay, mottle infection. The young fruit of these tomatoes are chosen optionally and divided into groups with marks, CHML-C is dilutes with distilled water from 35 mg 0/00 to 50 mg 0/00. The tomatoes are coated with the CHML-C for prophylaxis. Dosage of CHML-C used on each young fruit is 20 µl. Once a week for 3 weeks. The ripe fruits are weighed. The results are shown as Table 10.

TABLE 10

| groups | Number of young fruit | CHML-C administered mg/100 | Number of gangrenous spot | P* | average size of gangrenous spot (cm) | P* | average wt. of each tomato (g) | P* |
|---|---|---|---|---|---|---|---|---|
| inspection (control) | 120 | — | 58 | — | 1.28 | — | 155 | — |
| experimental (1) | 120 | 35 | 14 | <0.01 | 0.34 | <0.01 | 184 | <0.01 |
| experimental (2) | 120 | 50 | 4 | <0.01 | 0.2 | <0.01 | 190 | <0.01 |

Note: *test of significance (t)

X. Inhibition of S-180 Sarcoma Cell (In Vitro) With Single Component CHML

Single component listed in Table 1 can be prepared to CHML with the process of this invention. They possess the molecular structure as formula (2). In this formula, there is the site can be bound to the anticarcinogenic pharmaceutical and the site for activate the membrane structure of cancer cells. Therefore any single component can be prepared into CHML and provides anticarcinogenic effect.

For example, oleic acid acts as single component of molecular lipid when it is prepared to CHML. Its inhibition rate of S-180 (in vitro) attained 34% after 240 min.

Materials and Method

CHML is prepared from oleic acid into 0.5% & 0.1% CHML solution according to the process of "heterogeneous molecular lipid rearrangement" in this invention.

Sarcoma cell S-180 is diluted with RPMI-1640 incubation liquid to $1 \times 10^6$ cells/ml of suspension. It is added into 24 test tubes separately, 1.5 ml per test tube, (total=24 test tubes). These test tubes are placed in a thermostatic water bath at 37 C. 8 test tubes as an experimental group (1), 0.5% oleic acid CHML solution 0.4 ml are added to each tube drop wise, and 8 tubes as another experimental group (2), 1% oleic acid CHML solution 0.4 ml are added to each tube dropwisely, the remained 8 tubes group are as control, 0.4 ml. of physiological salt solution is added.

One test tube of every groups is taken out separately at intervals of 10 min., 20 min., 40 min., 60 min., 80 min., 100 min and 120 min., centrifuged and counted for the numbers of S-180 cells and form smears by Wright's staining method.

The results are shown in Table 11.

TABLE 11

| group | oleic acid CHML mg/ml | mortality of S-180% | | | | | | | |
|---|---|---|---|---|---|---|---|---|---|
| | | 10 min | 20 min. | 40 min. | 60 min. | 80 min. | 100 min. | 100 min. | 240 min. |
| control | — | — | — | — | — | — | — | — | — |
| experimental | | | | | | | | | |
| (1) | 2 | — | 2 | 4 | 8 | 16 | 22 | 30 | 31 |
| (2) | 4 | — | 3 | 5 | 10 | 18 | 26 | 32 | 34 |

Stearic acid or vitamin D selected from Table 1 is used as the single component of CHML. 0.5% and 1% CHML solution are prepared separately, according to the process of "molecular lipid rearrangement. The procedure for the inhibition test of S-180 sarcoma cell is performed as above, experimental results are listed in Tables 12 and 13.

TABLE 12

| group | stearic acid CHML mg/ml | mortality of S-180% | | | | | | | |
|---|---|---|---|---|---|---|---|---|---|
| | | 10 min. | 20 min. | 40 min. | 60 min. | 80 min. | 100 min. | 100 min. | 240 min. |
| control | — | — | — | — | — | — | — | — | — |
| experimental | | | | | | | | | |
| (1) | 2 | | | | 3 | 5 | 7 | 12 | 14 |
| (2) | 4 | | | | 4 | 11 | 12 | 16 | 18 |

TABLE 13

| group | Vit D CHML mg/ml | mortality of S-180% | | | | | | | |
|---|---|---|---|---|---|---|---|---|---|
| | | 10 min. | 20 min. | 40 min. | 60 min. | 80 min. | 100 min. | 100 min. | 240 min. |
| control | — | — | — | — | — | — | — | — | — |
| experimental (1) | 2 | — | — | — | — | 2 | 4 | 7 | 8 |
| experimental (2) | 4 | — | — | — | — | 3 | 6 | 8 | 11 |

Results of inhibition of S-180 with prostaglandin E-CHML in vitro

| group | CHML content mg/dl | number of test tubes | 10 | 20 | 40 | 60 | 80 | 100 | 120 | 240 |
|---|---|---|---|---|---|---|---|---|---|---|
| control | — | 8 | — | — | — | — | — | — | — | — |
| experimental (1) | 2 | 8 | — | — | 1 | 2 | 16 | 24 | 38 | 40 |
| experimental (2) | 4 | 8 | — | — | 2 | 5 | 20 | 28 | 42 | 44 |

XI. Studies on Pharmacokinetics of CHML-Y Preparation in Animals 16 healthy mice (kun-ming sps.) are selected and optionally divided into 4 groups. 4 mice per group, average body weight about 20 g. the experimental groups is injected into to caudal vein (I.V.) with 25 mg/ml. 99 mTc- CHML-Y 0.5 ml. 0.5 ml of physiological salt solution is injected in the control group. After injections, during the interval of 2 hrs, 24 hrs and 72 hrs, the blood 0.5 ml is taken from their orbits and then liver, spleen, lung, stomach and brain tissue are dissected, accurately weighed and put into test tubes to determine the intensity of radiation of every tissue by scintillation counter.

The results are expressed in the radioactive pulse percentage per gram of various organ tissue occupies the pulse percentage of all organ tissue. These results are shown in Table 14.

TABLE 14

| groups | total pulse % | blood | liver | spleen | kidney | lung | stomach | brain |
|---|---|---|---|---|---|---|---|---|
| control | — | — | — | — | — | — | — | — |
| 2 hrs. | 100 | 9 | 65 | 16 | 4 | 4.5 | 0.5 | 1 |
| 24 hrs. | 67.2 | 4 | 40 | 12 | 8 | 3 | 1.2 | — |
| 72 hrs. | 6 | — | 3 | 2 | 1 | — | — | — |

The results of animal tests shown in Table 14, show after i.v. injection of CHML-Y 2 hrs, the pharmaceutical distributes into liver, spleen, kidney, lung and brain 2 hrs. The absorption in liver is highest. The next are in lung, spleen and kidney. The levels in the stomach and brain are in minimum. After 24 hrs. metabolism products of CHML-Y excreted from the kidney are about 32%, but there is a high retention in liver and spleen. After 72 hrs. metabolism products of CHML-Y excreted from body are 94%, only trace amount retained in liver, spleen and kidney.

Effect of CHML-H Preparations on Hypertension of Rats

36 Wister rats, male, (average body weight 175 g), are divided into groups. 12 rats acts as normal group, the right kidney of the remained 24 rats are cut off. Doca oil preparation 30 mg/kg is injected subcutaneously. They are further divided into hypertension group, anti-hypertension group (1) and anti hypertension group (2), 8 rats per group. The normal group and hypertension group are fed with normal standard forage, the group of antihypertension (1) and (2) are fed with normal standard forage plus 5 mg/day & 10 mg/day of CHML-H preparation respectively. Prior and post to the experiment, the blood pressure is measured by a digital sphygmomanometer (measured by clamping on its tail).

The results are shown in Table 15.

TABLE 15

| groups | CHML-H dosage mg/day | numbers of animals (initial/final) | 2 weeks | 4 weeks | 6 weeks | 8 weeks |
|---|---|---|---|---|---|---|
| | | | \multicolumn{4}{c}{Blood pressure (mm Hg) prior to therapy} | | | |
| normal | — | 12/12 | 130 ± 2.1 | 130 ± 2.4 | 130 ± 1.7 | 130 ± 2.2 |
| hypertension (control) | — | 8/8 | 134 ± 2.3 | 144 ± 3.7 | 164 ± 4.6 | 170 ± 5.3 |
| antihypertension (1) | 5 | 8/8 | 134 ± 2.7 | 144 ± 4.1 | 163 ± 6.1 | 171 ± 4.8 |
| antihypertension (2) | 10 | 8/8 | 133 ± 3.9 | 145 ± 4.1 | 162 ± 8.1 | 171 ± 4.5 |
| | | | \multicolumn{4}{c}{Blood pressure (mm Hg) after therapy} | | | |
| normal | — | 12/12 | 130 ± 2.3 | 130 ± 2.2 | 130 ± 2.3 | 130 ± 2.4 |
| hypertension (control) | — | 8/8 | 173 ± 6.1 | 174 ± 5.1 | 167 ± 6.4 | 178 ± 5.6 |
| antihypertention (1) | 5 | 8/8 | 168 ± 5.3 | 164 ± 5.8 | 141 ± 4.5 | 136 ± 3.7* |
| antihypertension (2) | 10 | 8/8 | 157 ± 6.0 | 151 ± 7.1 | 133 ± 3.4 | 124 ± 2.5* |

Note *$P < 0.01$ (test of significance)

XIII. Effect of CHML-H on Hyperlipidemia in Rats

Material and method

Cholesterol oxidase is provided by Shanghai Institute of Pharmaceutical Industry, Biochemical department.

Reagent for separating high density protein subcomponent is provided by Shanghai cardiovascular disease Institute.

Wister rats, male, (average body weight about 115 g) are fed 3 days for inspection. Their blood are taken from their caudal vein and the content of total cholesterol (TC), high density lipoprotein cholesterol (HDL-C), low density lipoprotein cholesterol (LDL-C) and very low density lipoprotein cholesterol (VLDL-C) are detected.

These rats are divided into groups according to the level of lipoprotein cholesterol optionally. The rats with too high level or too low level of lipoprotein are disposed of.

The levels of lipoprotein cholesterol within every groups are almost equivalent to each other.

The experimental procedure is performed as follows.

Normal group: fed with conventional forage.

Hyperlipidemia group (control): fed with high lipid forage containing 10% cholesterol, 5% lard, 0.2% cholate.

Experimental group (1) fed with same forage as that of the hyperlipidemia group, but CHML-H preparation 5 mg/day is fed simultaneously.

Experimental group (2) fed with same forage as that of the hyperlipidemia group, but CHML-H preparation 10 mg/day is fed simultaneously.

After 10 days and 20 days for treatment, that blood are taken from caudal vein respectively for the detection of above items.

The experimental results are shown in Table 16.

TABLE 16

| groups | CHML-H dosage mg/day | number of animals initial/final | 0 | 10 days | 20 days |
|---|---|---|---|---|---|
| | | | \multicolumn{3}{c}{TC (mg/dl)} | | |
| normal | — | 12/12 | 78.8 ± 11.6 | 69.3 ± 10.4 | 68.3 ± 5.8 |
| hyperlipoidoma (control) | — | 10/10 | 72.5 ± 14.6 | 380.7 ± 103.2 | 402.3 ± 112.6 |
| experimental (1) | 5 | 10/10 | 75.4 ± 10.5 | 187.4 ± 87.4 | 198.7 ± 32.4* |
| experimental (2) | 10 | 10/10 | 79.5 ± 11.4 | 139.5 ± 54.7 | 148.5 ± 39.8* |
| | | | \multicolumn{3}{c}{HDL-C (mg/dl)} | | |
| normal | — | 12/12 | 47.7 ± 4.8 | 45.5 ± 5.9 | 44.1 ± 3.5 |
| hyperlipoidoma (control) | — | 10/10 | 46.8 ± 10.3 | 26.4 ± 6.8 | 22.9 ± 7.6 |
| experimental (1) | 5 | 10/10 | 47.9 ± 8.4 | 34.5 ± 10.9 | 38.8 ± 11.5* |
| experimental (2) | 10 | 10/10 | 46.5 ± 11.2 | 38.4 ± 9.8 | 39.5 ± 8.9* |
| | | | \multicolumn{3}{c}{LDL-C (mg/dl)} | | |
| normal | — | 12/12 | 27.2 ± 4.5 | 14.5 ± 7.4 | 140.7 ± 5.7 |
| hyperlipoidema (control) | — | 10/10 | 26.5 ± 5.4 | 278.1 ± 91.4 | 241.5 ± 75.4 |
| experimental (1) | 5 | 10/10 | 25.5 ± 7.8 | 139.8 ± 88.9* | 191.2 ± 60.7* |
| experimental (2) | 10 | 10/10 | 25.8 ± 6.9 | 132.5 ± 51.4* | 89.3 ± 42.5* |
| | | | \multicolumn{3}{c}{VLDL-C (mg/dl)} | | |
| normal | — | 12/12 | 12.9 ± 5.1 | 12.2 ± 2.8 | 11.8 ± 2.9 |
| hyperlipoidema | — | 10/10 | 12.2 ± 4.5 | 83.5 ± 22.7 | 141.2 ± 90.4 |
| experimental (1) | 5 | 10/10 | 14.2 ± 4.9 | 45.7 ± 19.5* | 60.1 ± 31.2* |

TABLE 16-continued

| groups | CHML-H dosage mg/day | number of animals initial/final | 0 | 10 days | 20 days |
|---|---|---|---|---|---|
| experimental (2) | 10 | 10/10 | 11.6 ± 6.2 | 34.3 ± 13.2* | 36.8 ± 18.2* |

Note: *P < 0.01 (test of significance t)

CHML-H exerts the functions for decreasing the level of the total cholesterol, low density lipoprotein cholesterol, (LDL-C) and very low density lipoprotein cholesterol (VLDL-C) in rats. The effect is enhanced with the increasing of dosage. In addition, CHML-H exerts the function for increasing the level of high density lipoprotein cholesterol (HLDC), the effect is enhanced with increasing of dosage also. These results suggest that the CHML-H preparation provide the function of decrease of the blood lipids and the antiarteriosclerosis in rats. These results provide the valid base of animal test for the clinical trial.

XIIII. Antitumor Effects of CHML-Y In Vivo Test.

1. Effect of CHML-Y on S-180 Ascites Sarcoma

Material: CHML-Y provided by inventor

Mice BalB/C, Kunning sp, is provided by Shanghai Second Medical University.

S-180 sarcoma strain provided by Shanghai Cancer Institute

Method: Mice are inoculated with S-180 ascites sarcoma strain according to the conventional method, and administered 0.5% CHML-Y by stomach perfusion. 8 times per day for 8 days continuously the ascites sarcoma are weighed and compared with control, the results are shown in following:

| Results groups | dosage (days) mg/kg | number of mice initial/final | body weight (g) | sarcoma weight (g) | inhibition rats (%) | P |
|---|---|---|---|---|---|---|
| control | —(×8)PO | 20/20 | 20.0/27.1 | 1.69 | — | — |
| experimental (1) | 500(×8)PO | 8/8 | 20.0/25.1 | 0.75 | 56 | <0.01 |
| experimental (2) | 350(×8)PO | 8/8 | 20.5/26.4 | 0.81 | 52 | <0.01 |
| experimental (3) | 250×(8)PO | 8/8 | 20.6/26.7 | 0.94 | 44 | <0.01 |

2 Effect of CHML-Y on S-180 Solid Sarcoma

Material: CHMY-Y is provided by inventor

Mice BalB/C Kunming sp. is provided by Shanghai Second Medical University.

S-180 sarcoma strains-provided by Shanghai Cancer Institute

Methods: Mice BalB/C are inoculated with S-180 sarcoma strains according to the conventional method, and administered with 0.5% CHML-Y by stomach perfusion, 8 times per day for 8 days continuously. The mice are dissected and the sarcoma are taken out, weighed and compared with the control. The results are shown as following.

| Results groups | dosage (days) mg/kg | number of mice initial/final | body weight (g) | sarcoma weight (g) | inhibition rats (%) | P |
|---|---|---|---|---|---|---|
| control | —(×8)PO | 18/18 | 21.0/25.3 | 2.17 ± 0.53 | — | — |
| experimental (1) | 500(×8)PO | 8/8 | 20.4/27.3 | 0.86 ± 0.32 | 60.4 | <0.01 |
| experimental (2) | 350(×8)PO | 8/8 | 20.4/06.0 | 1.14 ± 0.44 | 47.5 | <0.01 |
| experimental (3) | 250(×8)PO | 8/8 | 20.3/25.4 | 1.41 ± 0.59 | 35.0 | <0.01 |

3. Effect of CHML-Y on S-180 Solid Sarcoma by Administration in Local Injection

Material same as above.

Method: Mice Balb/c are inoculated with S-180 sarcoma cells according to the conventional method, and administered with 0.5% CHML-Y by injected into the local site (duration: 4 times per day, administered period=8 days), the mice are dissected, the sarcoma are taken out, weighed, compared with the control.

| Results groups | dosage (days) mg/kg | number of mice initial/final | body weight (g) | sarcoma weight (g) | inhibition rats (%) | P |
|---|---|---|---|---|---|---|
| control | —inj. in local site | 18/18 | 20.4/28.3 | 1.30 ± 0.61 | — | — |
| experimental (1) | 500inj. in local site | 8/8 | 21.0/25.3 | 0.37 ± 0.32 | 82.6 | <0.01 |

-continued

| groups | Results dosage (days) mg/kg | number of mice initial/ final | body weight (g) | sarcoma weight (g) | inhibition rats (%) | P |
|---|---|---|---|---|---|---|
| experimental (2) | 350inj. in local site | 8/8 | 20.5/26.1 | 0.47 ± 0.70 | 77.9 | <0.01 |
| experimental (3) | 240inj. in local site | 8/8 | 20.8/26.6 | 0.66 ± 0.53 | 69.0 | <0.01 |

Discussion:

The therapeutic effects in animals are shown in above results by the CHML-Y preparation in this invention in vivo.

It provides significant antitumor effects. The inhibition rates are depend upon the dosage administered.

There results show that the CHML with very small sizes can attack to the cancer cell to become fragments. It is further proved that the CHML provides the function of molecular missile in its actual effects.

XV. Preliminary Study for the Prophylaxis Against the Precancerosis of Squamosum Carcinoma with CHML-V 1. Materials and methods A. The properties of CHML-V and method of treatment. CHML-V is a slight yellow liquid, soluble in water, gas and liquids, it forms a gel solution in water as shown by Tyndall phenomenon, their molecular sizes are 20-30 Å. It is preserved at ambient temperature with protection from light. It is synthesized and provided by inventor.

Specification: Each ampoule content: 50 mg CHML-V/ml.

Method of treatment: A week is a course for treatment, once a week. It locally injected into basis of site of precancerosis of squamosum carcinoma with CHML-V. Its dosage is 25 mg/10m based on size of precancerosis tissue.

B. The condition for Use of Vit. A Pills in Control Group

Vit. A pills were manufactured by Shanghai Dong Hai pharmaceuticals works, 25000/pill. The patients orally are administered Vit. A continuously in the examination period, 3 times daily, 1 pill per time.

C. The Condition of Patients for Clinical Trial Group and Control Group

Patients came from local outpatients, 16–72 years old, optionally divided into 2 groups. They were bearing non typical squama hyperplasia in epithelial layer at I-II stage. It was diagnosed by clinic and biopsy.

These patients had no serious disease in heart, liver and kidney. They were not under treatment in the zone of precancerosis.

D. The Methods and Standards for Distinguishing Effects

The methods for distinguishing effects:
a. Subject symptom: examined by inspection.
b. Examined by pathological section.
c. Biopsy of tissue.

The standard for distinguishing effects.
a. Healing: The symptoms of patient are disappeared, his mucosa is smooth (in normal). A normal squamous epithelium is ascertained by pathological examination and biopsy.
b. Obvious efficacy: the symptoms are disappeared, the precancerosis of mucosa is improved significantly by direct inspection. It exhibits as a chronic inflammation by pathological examination.
c. Therapeutic efficacy: The symptoms are improved, the appearance of mucosa is better than before. The extent of nontypical hyperplasia is reduced from III-II to II-I.
d. inefficacy: the symptoms show no variation or not significantly improvement. There are no changes in pathological examination during prior-and post-administration.
e. Exacerbation: The symptoms are the exacerbation or are heavier than prior-treatment, and the nontypical hyperplasia converted from precancerosis into carcinoma by pathological examination.

2. Results:

TABLE 1

| 1. The statistics of patients ||||||||||||
|---|---|---|---|---|---|---|---|---|---|---|---|
| groups | No. of cases | men | women | precanceposis in gum of teeth |||| precanceposis mucosa on cheek ||||
| | | | | I | II | III | % | I | II | III | % |
| therapeutic (CHML treated) | 23 | 11 | 12 | 3 | 3 | 0 | 26.1 | 3 | 4 | 0 | 30.4 |
| control | 24 | 10 | 14 | 4 | 3 | 0 | 29.2 | 4 | 4 | 0 | 33.3 |

| groups | No. of cases | men | women | precanceposis on tongue |||| precanceposis on lips |||| precanceposis on plate ||||
|---|---|---|---|---|---|---|---|---|---|---|---|---|---|---|---|
| | | | | I | II | III | % | I | II | III | % | I | II | III | % |
| therapeutic (CHML treated) | 23 | 11 | 12 | 2 | 2 | 1 | 21.7 | 3 | 1 | 0 | 17.4 | 1 | 0 | 0 | 4.3 |
| control (Vit. A | 24 | 10 | 14 | 2 | 3 | 0 | 20.8 | 2 | 2 | 0 | 16.7 | 0 | 0 | 0 | 0 |

TABLE 1-continued

| 1. The statistics of patients |
|---|
| treated) |

TABLE 2

2. The comparison of therapeutic efficacy between 2 groups.

| groups | cases treated | healing % | obvious efficacy | efficacy % | inefficacy % | exacerbation % |
|---|---|---|---|---|---|---|
| CHML-treated | 23 | 17 73.9 | 4 17.4 | 1 4.35 | 1 4.35 | 0 0 |
| Vit. A treated (control) | 24 | 3 12.5 | 2 8.3 | 3 12.5 | 9 37.5 | 7 29.2 |

$X^2 0.05(1) = 3.841$
$X^2 0.01(1) = 6.635$
$X^2 = 17.15$
$P < 0.01$

TABLE 3

3. The course and effect of therapeutic group with CHML.

| course | cases treated | healing | obvious efficacy | efficacy | inefficacy | exacerbation |
|---|---|---|---|---|---|---|
| I | 23 | 10 | 5 | 6 | 2 | 0 |
| II | 13 | 5 | 5 | 2 | 1 | 0 |
| III | 8 | 2 | 4 | 4 | 1 | 0 |

In addition to the above experiments, the CHML compositions of the present invention were used to successfully treat 5 cancer patients in the People's Republic of China. These patients were clinically diagnosed with tumors including: granuloma fungoides (Stage III), melanocarcinoma and pigmentary basaloma. Further, one of the compositions of the present invention, CHML-Y2 (X radical is calcium), was tested by the National Cancer Institute Pre-clinical Anti-tumor Drug Discovery Screen and shown to be effective in vitro for small cell lung cancer, in particular. Still further, the present inventor has tested CHML compositions in vitro on Lewis lung carcinoma (LL/2), HeLa, sarcoma-180 (S-180) and human lung carcinoma (A549) cell lines. In these tests, the CHML compositions were evaluated for cytotoxicity and cancer cell inhibition. The results showed that the CHML compositions were more cytotoxicity to the cancer cells that the normal cells, and that it appeared that the CHML caused cancer cell membranes to atrophy and break, while also observing the nuclei of cancer cells to rupture.

From the large amount of experimental results, the "molecular missile" CHML in this clinical trial is an effective pharmaceutical carrier, not only in theoretical consideration but the actual effects appeared also. For example, CHML molecular lipid bind to the membrane of cancer cell specially, cancer is due to the function of sodium pump of the membrane of cell is in sthenic state, micro viscosity is increased, CHML can attack accurately to the target cell. According to the above experimental results and photographs, it can be seen that CHML with very small sizes can attack to the cancer to become fragments. It is further proved that the CHML provides the function of "molecular missile" in its actual effects.

Descriptions as above, include all the special terms, examples and figures, there is only for illustration of specificity of this invention in some extent. This total description is only for illustration and by no means of limitation.

However, it can be understood that there may be many modifications and variations in the changes of different forms, sizes, structures, components, purities and compositions of the present invention. However, applicant do intend to include all such obvious modifications and variations within the scope of the invention which is defined by the following claims to be protected.

What is claimed is:

1. A pharmaceutical composition, comprising:
   0.5-2.0 wt. % squalene;
   64.2-123.5 wt. % unsaturated fatty acids;
   11.5-22 wt. % saturated fatty acids;
   3.0-7.0 wt % Vitamin E;
   0-0.5 wt % Vitamin D; and
   0-0.5 wt % Vitamin A;
prepared by homogenizing the compounds listed above, heating the mixture to 293°-303° K., filtering the mixture through a 0.6µ membrane, adding activated carbon to the filtrate and heating to boiling for 30-60 minutes, decreasing the temperature to 288°-303° K. and filtering through a 0.45µ membrane, ultracentrifuging the filtrate, and filtering the centrifugate through a 0.025µ membrane, thereby obtaining a transparent composition.

2. The pharmaceutical composition of claim 1, which comprises:
   0.5-2.0 wt. % squalene;
   0.7-2.5 wt. % τ-linoleinic acid;
   1.0-4.0 wt. % linolenic acid;
   14-28 wt. % oleic acid;
   5-10 wt. % stearic acid;
   6.5-12 wt. % palmitic acid;
   3-7 wt. % eicosatetraenoic acid;
   8-11 wt. % eicosapentaenoic acid;
   2-4 wt. % eicosatrienoic acid;
   10-15 wt. % docosahexenoic acid;
   2-4 wt. % tetracosenoic acid;
   4-6 wt. % docosenoic acid;
   0.5-2 wt. % docosadienoic acid;
   1-3 wt. % docosatrienoic acid;
   3-7 wt. % docosatetraenoic acid;
   5-10 wt. % docosapentaenoic acid;
   10-20 wt. % palmitoleic acid;
   3-7 wt. % Vitamin E;
   0-0.5 wt. % Vitamin D; and
   0-0.5 wt. % Vitamin A.

3. A method for treating small cell lung cancer, Sarcoma-180, Lewis lung carcinoma, human lung carcinoma, HeLa cell cancer, melanoma, granuloma fungoides, squamous carcinoma or pigmentary basaloma, comprising administering an effective amount of a composition comprising:
   0.5-2.0 wt. % squalene;
   64.2-123.5 wt. % unsaturated fatty acids;
   11.5-22 wt. % saturated fatty acids;
   3.0-7.0 wt % Vitamin E;
   0-0.5 wt % Vitamin D; and
   0-0.5 wt % Vitamin A;

said composition being prepared by homogenizing the compounds listed above, heating the mixture to 293°–303° K., filtering the mixture through a 0.6μ membrane, adding activated carbon to the filtrate and heating to boiling for 30–60 minutes, decreasing the temperature to 288°–303° K. and filtering through a 0.45μ membrane, ultracentrifuging the filtrate, and filtering the centrifugate through a 0.025μ membrane, thereby obtaining a transparent composition.

4. The method of claim 3, wherein the composition comprises:
- 0.5–2.0 wt. % squalene;
- 0.7–2.5 wt. % τ-linolenic acid;
- 1.0–4.0 wt. % linolenic acid;
- 14–28 wt. % oleic acid;
- 5–10 wt. % stearic acid;
- 6.5–12 wt. % palmitic acid;
- 3–7 wt. % eicosatetraenoic acid;
- 8–11 wt. % eicosapentaenoic acid;
- 2–4 wt. % eicosatrienoic acid;
- 10–15 wt. % docosahexenoic acid;
- 2–4 wt. % tetracosenoic acid;
- 4–6 wt. % docosenoic acid;
- 0.5–2 wt. % docosadienoic acid;
- 1–3 wt. % docosatrienoic acid;
- 3–7 wt. % docosatetraenoic acid;
- 5–10 wt. % docosapentaenoic acid;
- 10–20 wt. % palmitoleic acid;
- 3–7 wt. % Vitamin E;
- 0–0.5 wt. % Vitamin D; and
- 0–0.5 wt. % Vitamin A.

* * * * *